United States Patent
Chu

(10) Patent No.: US 8,673,926 B2
(45) Date of Patent: Mar. 18, 2014

(54) SPIRO[2.4]HEPTANES FOR TREATMENT OF FLAVIVIRIDAE INFECTIONS

(71) Applicant: University of Georgia Research Foundation, Inc., Athens, GA (US)

(72) Inventor: Chung K. Chu, Statham, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 13/767,042

(22) Filed: Feb. 14, 2013

(65) Prior Publication Data

US 2013/0224152 A1    Aug. 29, 2013

Related U.S. Application Data

(60) Provisional application No. 61/598,524, filed on Feb. 14, 2012, provisional application No. 61/615,975, filed on Mar. 27, 2012, provisional application No. 61/615,989, filed on Mar. 27, 2012.

(51) Int. Cl.
  *A01N 43/90* (2006.01)
  *A61K 31/53* (2006.01)

(52) U.S. Cl.
  USPC ............... 514/263.1; 514/263.37; 514/274; 544/277; 544/265; 544/304; 544/317

(58) Field of Classification Search
  USPC .......... 514/263.1, 263.37, 274; 544/277, 265, 544/304, 317
  See application file for complete search history.

(56) References Cited

U.S. PATENT DOCUMENTS

| | | | |
|---|---|---|---|
| 6,348,587 B1 | 2/2002 | Schinazi et al. |
| 6,455,513 B1 | 9/2002 | McGuigan et al. |
| 6,777,395 B2 | 8/2004 | Bhat et al. |
| 6,812,219 B2 | 11/2004 | LaColla et al. |
| 6,911,424 B2 | 6/2005 | Schinazi et al. |
| 6,914,054 B2 | 7/2005 | Sommadossi et al. |
| 6,949,522 B2 | 9/2005 | Otto et al. |
| 7,105,493 B2 | 9/2006 | Sommadossi et al. |
| 7,105,499 B2 | 9/2006 | Carroll et al. |
| 7,125,855 B2 | 10/2006 | Bhat et al. |
| 7,148,206 B2 | 12/2006 | Sommadossi et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,202,224 B2 | 4/2007 | Eldrup et al. |
| 7,307,065 B2 | 12/2007 | Schinazi et al. |
| 7,365,057 B2 | 4/2008 | LaColla et al. |
| 7,429,572 B2 | 9/2008 | Clark |
| 7,456,155 B2 | 11/2008 | Sommadossi et al. |
| 7,547,704 B2 | 6/2009 | LaColla et al. |
| 7,608,597 B2 | 10/2009 | Sommadossi et al. |
| 7,608,600 B2 | 10/2009 | Storer et al. |
| 7,625,875 B2 | 12/2009 | Gosselin et al. |
| 7,635,689 B2 | 12/2009 | LaColla et al. |
| 7,662,938 B2 | 2/2010 | Schinazi et al. |
| 7,879,815 B2 | 2/2011 | MacCoss et al. |
| 7,902,202 B2 | 3/2011 | Sommadossi et al. |
| 7,951,789 B2 | 5/2011 | Sommadossi et al. |
| 7,964,580 B2 | 6/2011 | Sofia et al. |
| 7,973,013 B2 | 7/2011 | Cho et al. |
| 8,071,568 B2 | 12/2011 | Narjes et al. |
| 8,093,380 B2 | 1/2012 | Wang et al. |
| 8,148,349 B2 | 4/2012 | Meppen et al. |
| 8,168,583 B2 | 5/2012 | Schinazi et al. |
| 8,299,038 B2 | 10/2012 | Sommadossi et al. |
| 8,324,179 B2 | 12/2012 | Chen et al. |
| 8,334,270 B2 | 12/2012 | Sofia et al. |
| 8,343,937 B2 | 1/2013 | Sommadossi et al. |

FOREIGN PATENT DOCUMENTS

| EP | 2120565 B1 | 11/2012 |
|---|---|---|
| WO | WO 00/32220 A1 | 6/2000 |
| WO | WO 2004/106356 A1 | 12/2004 |

OTHER PUBLICATIONS

Oh et al., 30 Nucleosides, Nucleotides & Nucleic Acids, 423-439 (2011).*
S. Gadthula et al., 21 Bioorganic & Medicinal Chemistry Letters, 3982-3985 (2011).*
Gadthula et al. "Synthesis and antiviral activity of cyclopropyl-spirocarbocyclic adenosine, (4R,5S,6R,7R)-4-(6-amino-9H-purin-9-yl)-7-(hydroxymethyl)spiro[2.4]heptane-5,6-diol against hepatitis C virus" Bioorganic & Medicinal Chemistry Letters, 21:3982-3985, 2011.
OH et al. "Design and Synthesis of Novel Carbocyclic Versions of 2'-Spirocyclopropyl Ribonucleosides as Potent Anti-HCV Agents" Nuclecosides, Nucleotides and Nucleic Acids, 30: 423-439, 2011.

* cited by examiner

*Primary Examiner* — James O Wilson
*Assistant Examiner* — Alexander R Pagano
(74) *Attorney, Agent, or Firm* — Knowles Intellectual Property Strategies, LLC

(57) ABSTRACT

Compounds, methods, and compositions for the treatment of infections in or exposure to humans and other host animals of Flaviviridae viruses, including HCV, that includes the administration of an effective amount of a spiro[2.4]heptane as described herein or a pharmaceutically acceptable salt or prodrug thereof, optionally in a pharmaceutically acceptable carrier, are provided. The spiro[2.4]heptane compounds either possess antiviral activity, or are metabolized to a compound that exhibits such activity.

27 Claims, 9 Drawing Sheets

R=H; NM107
R=Valine; NM283

R=H; R1479
R=COCH(CH$_3$)$_2$; R1626

R=H; PSI6130
R=COCH(CH$_3$)$_2$; R7128

IDX184

PSI7977

PSI938

US 8,673,926 B2

SPIRO[2.4]HEPTANES FOR TREATMENT OF FLAVIVIRIDAE INFECTIONS

RELATED APPLICATIONS

This application claims the benefit of priority of U.S. Provisional Application Ser. No. 61/615,989, filed Mar. 27, 2012, U.S. Provisional Application Ser. No. 61/615,975, filed Mar. 27, 2012, and U.S. Provisional Application Ser. No. 61/598,524, filed Feb. 14, 2012, the contents of which are incorporated herein by reference.

GOVERNMENT INTEREST

This invention was made with government support under grant AI25899 awarded by the U.S. Public Health Service, National Institute of Allergy and Infectious Diseases, NIH. The government has certain rights in the invention.

FIELD OF THE INVENTION

The present invention is in the field of compounds and their uses and compositions to treat viral infections, especially Flaviviridae viruses, including Hepatitis C Virus (HCV), as well as other related conditions.

BACKGROUND OF THE INVENTION

Flaviviridae are a family of RNA viruses with a single stranded positive sense RNA genome. The RNA viral genome plays important roles during viral replication, including as mRNA for viral protein synthesis, a template for RNA replication, and a nascent RNA genome for a newly formed virus. The family includes the genera Flavivirus, Hepacivirus, Hepatitis G Virus, and Pestivirus.

Major diseases caused by Flaviviridae include hepatitis C, Dengue fever, West Nile encephalitis, Tick-borne encephalitis, and Yellow fever.

Hepatitis C(HCV) is a Hepacivirus. It is estimated that 75% of all cases of liver disease is caused by HCV. HCV infection can lead to cirrhosis and liver cancer and can become so serious that a liver transplant is required. Approximately 170-200 million people worldwide are infected, with 3-5 million in the United States.

The HCV non-structural protein NS5B RNA-dependent RNA polymerase is a key component of the replicative complex and is responsible for initiating and catalyzing viral RNA synthesis. As a result, the HCV NS5B is an attractive target for the current drug discovery and development of anti-HCV agents. There are two major subclasses of NS5B inhibitors: nucleoside analogs, which are anabolized to their active triphosphates, and which act as alternative substrates for the polymerase, and non-nucleoside inhibitors (NNIs), which bind to allosteric regions on the protein. Nucleoside or nucleotide inhibitors mimic natural polymerase substrate and act as chain terminators. They inhibit the initiation of RNA tranclation and elongation of a nacent RNA chain.

Other HCV proteins that are targets for therapeutic approaches are NS3/4A (a serine protease) and NS5A (a non-structural protein that is an essential component of HCV replicase and exerts range of effects on cellular pathways).

Current approved therapies for HCV include interferon alpha-2b or pegylated interferon alpha-2b (Pegintron), which is administered with ribavirin (Rebetol), and NS3/4A protease inhibitors telaprevir (Incivek, Vertex and Johnson & Johnson) and boceprevir (Victrelis, Merck).

Several NS5B nucleoside/nucleotide polymerase inhibitors have been in clinical trials (shown in FIG. 1). 2'-C-methylcytidine (NM107), the valine ester of 2'-C-methylcytidine (valocitabine, NM283), was the first polymerase inhibitors in clinical trials and was discontinued due to the GI toxicity. The second nucleoside inhibitor, 4'-C-azido-nucleoside (R1479) as its tri-isobutyl ester prodrug (R1626), has been developed by Roche, however, it was discontinued due to the haematopoetic toxicity. Currently, Roche and Pharmasset are developing R7128 (mericitabine), a prodrug of β-D-2'-deoxy-2'-α-fluoro-2'-C-methylcytidine (PSI6130). Idenix has been developing a purine analogue, 2'-C-methylguanosine monophosphate prodrug (IDX184), however, it is currently under clinical hold due to the potential cardiac toxicity concern by the FDA because of the discontinuation of Inhibitex INX-189 due to cardio-toxicity. A uridine analogue in a prodrug (PSI-7977) form can potently inhibit HCV replication. Recently, a 3',5'-cyclic phosphate analogue, PSI-938, has also been reported as a potent anti-HCV agent but has been discontinued due to liver toxicity.

Oh et al. published an article on "Design and Synthesis of Novel Carbocyclic Versions of 2'-Spirocyclopropyl ribonucleosides as potent anti-HCV agents." Oh et al. reported that the synthesized cytosine nucleoside had moderate anti-HCV activity ($IC_{50}$ of 14.4 in Hu7 cell line).

Gadthula et al. published an article on "Synthesis and antiviral activity of cyclopropy-spirocarbocyclic adenosine (4R,5S,6R,7R)-4-(6-amino-9H-pur-9-yl)-7-(hydroxymethyl)spiro[2.4]heptane-5,6 diol against hepatitis C virus" (*Bioorganic & Medicinal Chemistry Letters* 21 (2011) 3982-3985). The titled compound exhibited an $EC_{50}$ of 0.273 and 0.368 µM in genotypes 1A and 1B, respectively in the Hu7 RNA replicon assay.

United States patents which describe nucleoside polymerase inhibitors for the treatment of Flaviviridae, including HCV, include those filed by Idenix Pharmaceuticals (U.S. Pat. Nos. 8,343,937; 8,299,038; 6,914,054; 6,812,219; 7,608,597; 7,902,202; 7,951,789; 7,547,704; 7,456,155; 7,365,057; 7,608,600; 7,635,689; 7,625,875; 7,148,206; 7,163,929; 7,169,766; 7,105,493; and 7,157,441), Merck (U.S. Pat. Nos. 7,125,855; 6,777,395; 7,105,499; and 7,202,224), Gilead Sciences (U.S. Pat. Nos. 7,973,013; 8,324,179; and 8,334,270), Emory University (U.S. Pat. Nos. 6,911,424; 8,168,583; 6,348,587; 7,662,938; and 7,307,065), and Pharmasset Inc. (U.S. Pat. Nos. 7,429,572; 8,093,380; 7,964,580; and 6,949,522).

There remains a strong medical need to develop anti-Flaviviridae, including anti-HCV, therapies that are effective, well-tolerated, and reasonably safe. Given the number of people infected with hepatitis C and the potential severity of the infection, the need is particularly strong. The need is accentuated by the expectation that combination drug therapies may be most efficacious to treat HCV and other Flaviviridae.

It is therefore an object of the present invention to provide compounds, pharmaceutical compositions, and methods and uses to treat and/or prevent infections from Flaviviridae viruses, including Hepatitis C virus, and related conditions and/or disease states as otherwise described herein.

BRIEF DESCRIPTION OF THE FIGURES

FIG. 2 Reagents and Conditions: (a) (Boc)₂O, DMAP, THF; 80% yield; (b) Savinase, THF, Buffer solution; 84% yield; (c) OsO₄, NMO, Acetone; 72% yield; (d) i) BzCl, Pyridine; 86% yield, ii) NaBH₄, Methanol; 83% yield; (e) HCl/Ether, Methanol; 90% yield; (f) NaNO₂, CH₃COOH, Water, Acetonitrile; 54% yield; (g) NaOMe, Methanol; 78% yield; (h) (i) 2,2-dimethoxy propane, PTSA, Acetone, (ii) TBDMSCl₂, Imidazole, DCM, (iii) mCPBA, DCM; 86% yield; (i) n-BuLi, trimethylsulfonium iodide, THF; (j) (i) Desmortine, DCM; (ii) NaBH₄, CeCl₃.7H₂O, MeOH; (k) Diethyl Zinc MeI₂, Ether; (l) Base, DIAD, TPP, THF; 70% yield; (m) TFA, TBAF/THF 90% yield; (n) Phosphoramidate chloride, NMI, THF; (o) DPPA, DIAD, TPP, THF; (p) methoxyacrylol isocyanate, THF; (q) NH₄OH, 1,4-dioxane/EtOH, steel bomb, 90-100° C.; (r) THF/H₂O; (s) Phosphoramidate chloride, NMI, THF.

FIG. 3 Reagents and Conditions: (a) BnCl, NaH, DMF; (b) TFA, TBAF/THF; (c) TBDMSCl₂, Imidazole, DCM; (d) DAST, DCM; (e) BCl₃, DCM; (f) Base, DIAD, TPP, THF; (g) TFA, TBAF/THF; (h) Base, DIAD, TPP, THF; (i) (i) NH₃/Methanol; (ii) TFA, TBAF/THF.

FIG. 4 Reagents and Conditions: (a) PCC, DCM; (b) BCl₃, DCM; (c) Base, DIAD, TPP, THF; (d) CH₃Li, THF; (e) DAST, DCM; (f) TFA, TBAF/THF.

FIG. 5 Reagents and Conditions: (a) BnCl, NaH, DMF; (b) TFA, TBAF/THF; (c) TBDMSCl₂, Imidazole, DCM (d) DAST, DCM; (e) BCl₃, DCM; (f) Base, DIAD, TPP, THF; (g) TFA, TBAF/THF.

FIG. 6 Reagents and Conditions: (a) i) NaNO₂, CH₃COOH, water Acetonitrile; ii) NaOMe, Methanol; (b) TIDPSCl₂, Imidazole, DCM; (c) mCPBA, DCM; (d) BzCl, Pyridine; (e) Trimethyl sulfonium Iodide, nBuLi, THF; (f) Diethyl Zinc, MeI, ether; (g) Base (Purine or pyrimidine), DIAD, TPP, THF; (h) NaOMe, Methanol; (i) TBAF, Acetic acid, THF; (j) PDC, DCM; (k) CH₃MgBr, ether; (l) TBAF, Acetic acid, THF; (m) DAST, DCM; (n) TBAF, Acetic acid, THF; (o) i) Tf₂O, Py; ii) CeOAc, benzene; (p) NaOMe, Methanol; (q) DAST, DCM; (r) TBAF, Acetic acid, THF.

FIG. 7 Reagents and Conditions: (a) Trimethyl sulfonium Iodide, nBuLi, THF; (b) Base (Purine or pyrimidine), DIAD, TPP, THF; (c) NaOMe, Methanol; (d) PDC, DCM; (e) CH₃MgBr, ether; (f) TBAF, Acetic acid, THF; (g) DAST, DCM; (h) TBAF, Acetic acid, THF.

FIG. 8 Reagents and Conditions: (a) i) NaNO₂, CH₃COOH, water Acetonitrile; ii) NaOMe, Methanol; (b) TIDPSCl₂, Imidazole, DCM; (c) mCPBA, DCM; (d) BzCl, Pyridine; (e) Trimethyl sulfonium Iodide, nBuLi, THF; (f) Base (Purine or pyrimidine), DIAD, TPP, THF; (g) NaOMe, Methanol; (h) TBAF, Acetic acid, THF; (i) PDC, DCM; (j) CH₃MgBr, ether; (k) TBAF, Acetic acid, THF; (l) DAST, DCM; (m) TBAF, Acetic acid, THF; (n) i) Tf₂O, Py; ii) CeOAc, benzene; (o) NaOMe, Methanol; (p) DAST, DCM; (q) TBAF, Acetic acid, THF.

FIG. 9 shows how to prepare β-L spiro[2.4]heptanes of the present invention.

FIG. 10 Reagents and Conditions: (a) Diethyl Zinc MeI₂, Ether; (b) BnCl, NaH, DMF; (c) (i) TFA, TBAF/THF; (ii) TBDMSCl₂, Imidazole, DCM; (d) PCC, DCM; (e) CH₃Li, THF; (f) DAST, DCM; (g) BCl₃, DCM; (h) Benzoic acid, DIAD, TPP, THF; (i) Base, DIAD, TPP, THF; (j) TFA, TBAF/THF.

FIG. 11 Reagents and Conditions: (a) CH₃Li, THF or CH₃MgCl, THF; (b) Actyl chloride, DIMAP, DCM; (c) BCl₃, DCM; (d) Base, DIAD, TPP, THF; (e) NaOMe, MeOH; (f) TFA, TBAF/THF.

SUMMARY OF THE INVENTION

Figure 1:
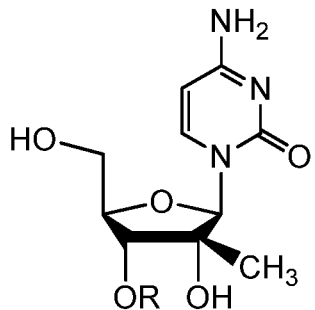
FIG. 1 shows a number of nucleoside/nucleotide polymerase inhibitors which are or have been in clinical trials.
Figure 1:
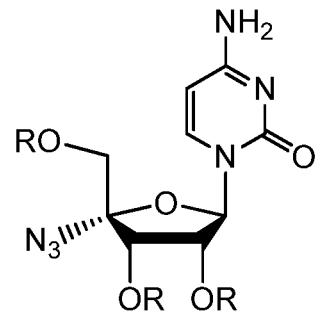
Figure 1:
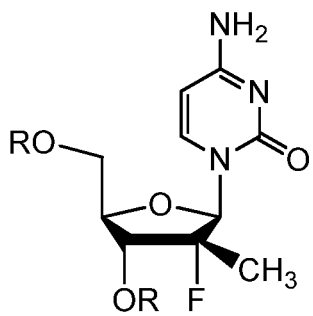
Figure 1:
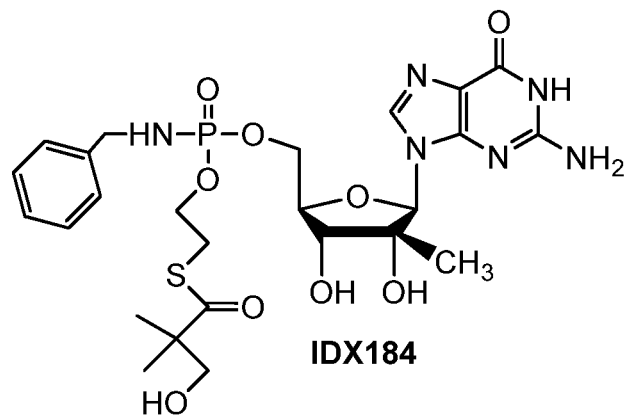
Figure 1:
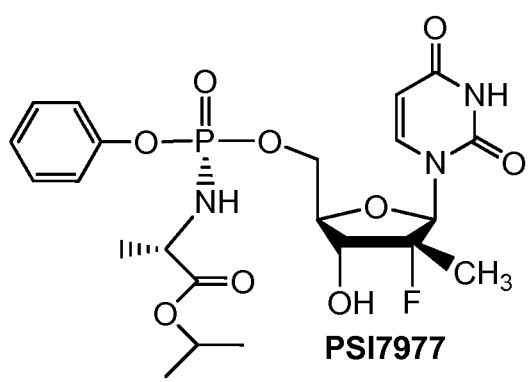
Figure 1:
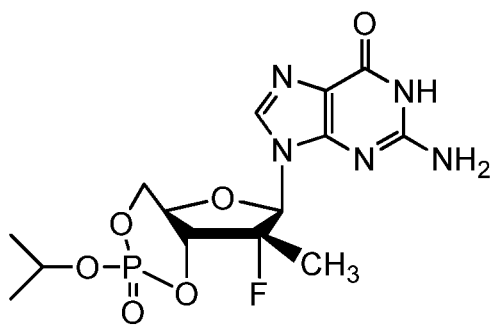

Compounds, methods, and compositions are provided for the treatment of a host infected with a Flaviviridae virus (for example, a Flavivirus, Hepacivirus, Hepatitis G Virus, or Pestivirus), and more particularly, Hepatitis C, Dengue fever, West Nile encephalitis, Tick-borne encephalitis, or Yellow fever. The compounds and compositions can also be used to treat related conditions such as anti-Flaviviridae (for example, anti-HCV) antibody positive and antigen positive conditions, viral-based chronic liver inflammation, liver cancer resulting from advanced hepatitis C, cirrhosis, chronic or acute hepatitis C, fulminant hepatitis C, chronic persistent hepatitis C and anti-Flaviviridae-based fatigue. The compound or formulations that include the compounds can also be used prophylactically to prevent or retard the progression of clinical illness in individuals who are anti-Flaviviridae (for example, anti-HCV) antibody or antigen positive or who have been exposed to a Flaviviridae, such as hepatitis C.

The invention includes using an effective amount for a host in need thereof of the spiro[2.4]heptane of Formula I or II (which have a β-D type configuration with reference to a corresponding nucleoside) or a pharmaceutically acceptable composition, salt, or prodrug thereof:

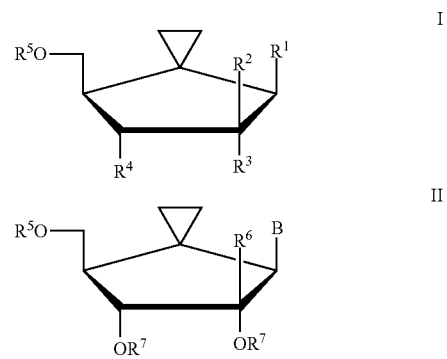

wherein:

$R^1$ is a natural or non-natural heteroaryl or heterocyclic moiety, which can be a pyrimidine or purine, for example cytosine, 5-halocytosine (for example, 5-fluorocytosine or 5-iodocytosine), uracil, 5-halouracil (for example, 5-fluorouracil or 5-iodouracil), 5-methylcytosine, thymine, adenine, thymine, guanine, xanthine, or hypoxanthine;

$R^2$ is $C_1$-$C_4$ alkyl or substituted alkyl (for example methyl), F, Cl, $N_3$, or $OR^7$;

$R^3$ is $C_1$-$C_4$ alkyl or substituted alkyl, (for example methyl), F, Cl, $N_3$, or $OR^7$;

$R^4$ is $OR^7$, H, $C_1$-$C_4$ alkyl (for example methyl), F, Cl, or $N_3$;

$R^5$ is H; phosphate (including mono-, di- or triphosphate or a stabilized phosphate prodrug); phosphoramidate; acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^5$ is H or (mono, di or tri) phosphate;

B is cytosine, 5-halocytosine (for example, 5-fluorocytosine or 5-iodocytosine), uracil, 5-halouracil (for example, 5-fluorouracil or 5-iodouracil), 5-methylcytosine, thymine, adenine, guanine, xanthine or hypoxanthine, or a non-natural heteroaryl or heterocyclic moiety'

$R^6$ is H; and, $R^7$ is H, acyl, phosphate, sulfate, amino acid, peptide, or an oxygen-protecting group.

In one embodiment, in Formula I, $R^2$ is H and $R^3$ is F.

In another embodiment, in Formula I either $R^3$ and $R^4$ or $R^4$ and $R^5$, or in Formula II $R^4$ and $R^5$ together form a bridge that may, for example, be a phosphoester, carbodiester or phosphoroamidate.

In an alternative embodiment, compounds, methods, and compositions are provided for the treatment of a host infected with or exposed to a Flaviviridae virus (Hepatitis C, Dengue fever, West Nile encephalitis, Tick-borne encephalitis, or Yellow fever) described herein. The invention includes using an effective treatment amount for a host of the spiro[2.4]heptane of Formula III or IV (with β-L type configuration with reference to a corresponding nucleoside) or a pharmaceutically acceptable composition, salt or prodrug thereof:

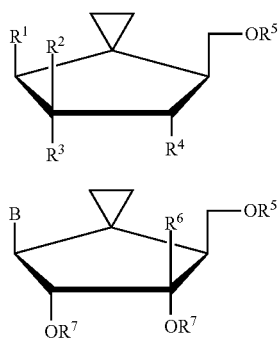

wherein $R^1$, $R^2$, $R^3$, $R^4$, $R^5$, $R^6$, $R^7$, and B are as defined above.

The compounds of the invention can be administered alone or in combination with another anti-Flaviviridae, for example an anti-HCV, drug to treat the infected host. In certain embodiments, it is useful to administer a combination of drugs that modulates a different pathway or inhibits a different target in the virus. Since the disclosed spiro[2.4]heptanes are NS5B polymerase inhibitors, it may be useful to administer the compound to a host in combination with a protease inhibitor, such as an NS3/4A protease inhibitor (for example, telaprevir (Incivek) or biceprevir (Victrelis) or an NS5A inhibitor. The compound of the invention can also be administered in combination with a structurally different NS5B polymerase inhibitor such as another compound described herein or below, including Gilead's PSI-7977 or Roche's PSI-7128. The compounds of the invention can also be administered in combination with interferon alfa-2a, which may be pegylated or otherwise modified, and/or ribavirin.

The spiro[2.4]heptanes of the invention are typically administered orally, for example in pill or tablet form, but may be administered via other routes which the attending physician considers appropriate, including via intravenous, transdermal, subcutaneous, topical, parenteral, or other suitable route.

DETAILED DESCRIPTION OF THE INVENTION

The invention disclosed herein is a compound, method, and composition for the treatment of infections in or exposure to humans and other host animals of the Flaviviridae viruses described herein or otherwise known, including HCV, that includes the administration of an effective amount of a spiro[2.4]heptane as described herein or a pharmaceutically acceptable salt or prodrug thereof, optionally in a pharmaceutically acceptable carrier. The compounds of this invention either possess antiviral activity, or are metabolized to a compound that exhibits such activity.

The compounds and compositions can also be used to treat related conditions such as anti-Flaviviridae antibody positive and Flaviviridae-antigen positive conditions, viral-based chronic liver inflammation, liver cancer resulting from advanced hepatitis C, cirrhosis, acute hepatitis C, fulminant hepatitis C, chronic persistent hepatitis C, and anti-Flaviviridae-based fatigue. The compounds or formulations that include the compounds can also be used prophylactically to prevent or retard the progression of clinical illness in individuals who are anti-Flaviviridae antibody or Flaviviridae-antigen positive or who have been exposed to a Flaviviridae, such as hepatitis C.

The present invention includes the following features:

(a) spiro[2.4]heptanes as described herein, and pharmaceutically acceptable salts and prodrugs thereof (in either the β-D- or β-L form when considered with respect to corresponding nucleoside structure);

(b) spiro[2.4]heptanes (with relative β-D- or β-L-configuration) as described herein, and pharmaceutically acceptable salts and prodrugs thereof for use in the treatment or prophylaxis of a Flaviviridae infection, for example a hepatitis C infection;

(c) use of spiro[2.4]heptanes (with relative β-D- or β-L-configuration), and pharmaceutically acceptable salts and prodrugs thereof in the manufacture of a medicament for treatment of a Flaviviridae, for example, a hepatitis C infection;

(d) a method for manufacturing a medicament intended for the therapeutic use for treating a Flaviviridae infection, for example, a hepatitis C infection, characterized in that a spiro[2.4]heptane (with relative β-D- or β-L-configuration) as described herein is used in the manufacture;

(e) a pharmaceutical formulation comprising an effective host-treating amount of the spiro[2.4]heptane (with relative β-D- or β-L-configuration) or a pharmaceutically acceptable salt or prodrug thereof together with a pharmaceutically acceptable carrier or diluent;

(f) spiro[2.4]heptane (with relative β-D- or β-L-configuration) as described herein substantially in the absence of the opposite enantiomer of the described compound, or substantially isolated from other chemical entities; and, (g) processes for the preparation of therapeutic products that contain an effective amount of a spiro[2.4]heptane (with relative β-D- or β-L-configuration), as described herein.

I. Spiro[2.4]Heptanes of the Invention

The spiro[2.4]heptanes of the invention are those depicted in Formula I or II or a pharmaceutically acceptable composition, salt or prodrug thereof:

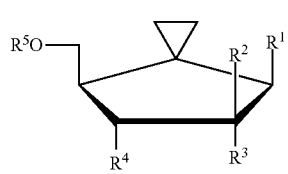

-continued

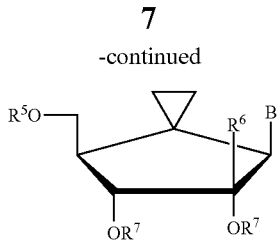

II

In an alternative embodiment, compounds, methods, and compositions are provided for the treatment of a host infected with or exposed to hepatitis C or another Flaviviridae virus (for example, Dengue fever, West Nile encephalitis, Tick-borne encephalitis, or Yellow fever). The invention includes using an effective treatment amount for a host of the spiro [2.4]heptane of Formula III or IV (with β-L type configuration with reference to a corresponding nucleoside) or a pharmaceutically acceptable composition, salt, or prodrug thereof:

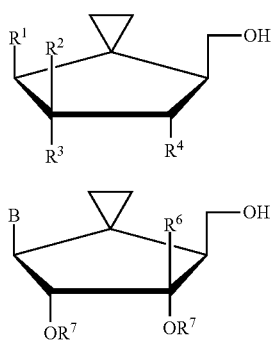

wherein:
$R^1$ is a natural or non-natural heteroaryl or heterocyclic moiety, which can be a pyrimidine or purine, for example cytosine, 5-halocytosine (for example, 5-fluorocytosine or 5-iodocytosine), uracil, 5-halouracil (for example, 5-fluorouracil or 5-iodouracil), 5-methylcytosine, thymine, adenine, thymine, guanine, xanthine or hypoxanthine;
$R^2$ is $C_1$-$C_4$ alkyl (for example methyl), F, Cl, $N_3$, or $OR^7$;
$R^3$ is $C_1$-$C_4$ alkyl (for example methyl), F, Cl, $N_3$, or $OR^7$;
$R^4$ is $OR^7$, H, $C_1$-$C_4$ alkyl (for example methyl), F, Cl, or $N_3$;
$R^5$ is H; phosphate (including mono-, di- or triphosphate or a stabilized phosphate prodrug); phosphoramidate; phosphonate; amino acid; acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; a carbohydrate; a peptide; a cholesterol; or other pharmaceutically acceptable leaving group which when administered in vivo is capable of providing a compound wherein $R^5$ is H or phosphate;
B is cytosine, 5-halocytosine (for example, 5-fluorocytosine or 5-iodocytosine), uracil, 5-halouracil (for example, 5-fluorouracil or 5-iodouracil), 5-methylcytosine, thymine, or a natural or non-natural heteroaryl or heterocyclic moiety;
$R^6$ is H; and,
$R^7$ is H; phosphate (including mono-, di- or triphosphate or a stabilized phosphate prodrug); phosphoramidate; phosphonate; amino acid; acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; a carbohydrate; a peptide; a cholesterol; or other pharmaceutically acceptable leaving group which when administered in vivo is capable of providing a compound wherein $R^5$ is H or phosphate.

In a typical embodiment, the compound is a β-D isomer with reference to the corresponding nucleoside (i.e., in the naturally occurring configuration). In an alternative configuration, the compound is provided as a β-L isomer. The compound is typically at least 95% free of the opposite enantiomer, and can be at least 98% or even 100% free of the opposite enantiomer.

In an embodiment, in Formula I, $R^2$ is H and $R^3$ is F.

In another embodiment, either $R^3$ and $R^4$ or $R^4$ and $R^5$ together form a bridge that may be, for example, a phosphoester, carbodiester, or phosphoramidate.

In another embodiment, either of the two —$CH_2$— groups in the cyclopropyl ring can have a substituent, for example, methyl, halogen (F, Cl, Br or I), —OH, or $N_3$. In general, if a substituent is placed on the cyclopropyl ring, it should be small due to potential steric hindrance in the position. Typically, the cyclopropyl group is unsubstituted.

In an embodiment, $R^1$ is a group according to the chemical formula $R_{1a}$ or $R_{1b}$:

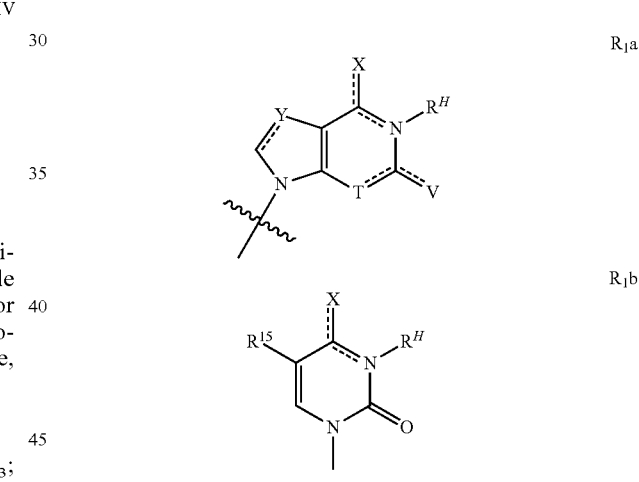

wherein:
X is H, —$NR^A R^B$, halogen (F, Cl, Br or I), O, $OR^X$, S or $SR^X$;
T is N—$R^W$ or C—$R^{WA}R^{WB}$;
V is H, O, $OR^X$, S or $SR^X$, a $C_1$-$C_3$ alkyl, a $NR^A R^B$ group, a halogen (F, Cl, Br, I), nitro, cyano,

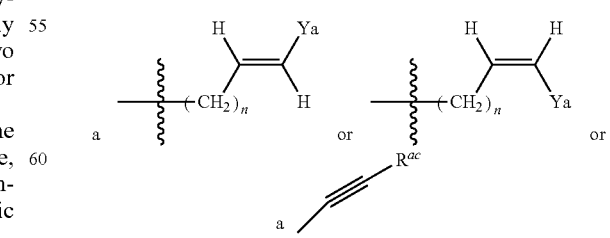

group;
Y is C—$R^Y$, N, O or S;
Ya is H, F, Cl, Br, I, or —$C_1$-$C_4$ alkyl;

$R^H$ is absent, H, or a $C_1$-$C_3$ alkyl;
$R^{15}$ is H, F, Cl, Br, I, $C_1$-$C_4$ alkyl (often $CH_3$), —C≡N, —$(CH_2)_n$C≡C—$R_a$,

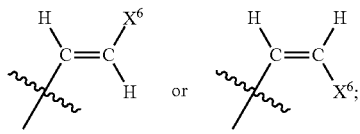

$X^6$ is H, $C_1$-$C_4$ alkyl (often, $CH_3$), F, Cl, Br, or I;
$R_a$ is H, F, Cl, Br, I, or —$C_1$-$C_4$ alkyl, often H or $CH_3$;
n is 0, 1, 2, 3, 4, 5 (often 0 or 1);
$R^W$ is absent, H, or a $C_1$-$C_3$ alkyl group;
$R^{WA}$ is H or a $C_1$-$C_3$ alkyl group;
$R^{WB}$ is absent, H, or a $C_1$-$C_3$ alkyl group;
$R^Y$ is H, a $C_1$-$C_3$ alkyl group, a halo group (F, Cl, Br or I), nitro, cyano, or a

group;
$R^A$, $R^B$, and $R^x$ are each independently H, an acyl group, a $C_1$-$C_{20}$ alkyl or ether group, or an amino acid residue (D or L); and
$R^{ac}$ is H or a $C_1$-$C_3$ alkyl group which is optionally substituted with 1 or 2 hydroxyl groups or from 1 to 3 halogens (when substituted, $R^{ac}$ is often substituted with 3 fluoro groups).

In certain aspects of the invention of any of the spiro[2.4]heptanes described herein, $R^1$ is according to the formula:

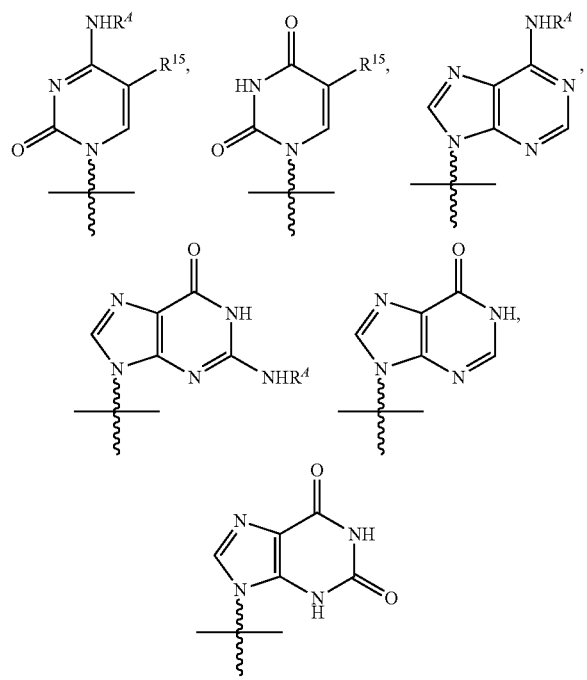

wherein $R^{15}$ and $R^A$ are the same as described above. $R^{15}$ is often H, $CH_3$, or F, more often H, and $R^A$ is an acyl group as otherwise described herein or a $C_1$-$C_6$ alkyl group, in certain instances, a cyclopropyl group.

In still other embodiments, $R_1$ is uracil, thymine, cytosine, 5-methylcytosine, 7-deazaadenine, guanine, xanthine, or hypoxanthine. In some embodiments, B is uracil, cytosine, or guanine. Alternatively, in certain embodiments, B is cytosine, uracil, thymine, or guanine, where $R^A$ is H, an acyl group, a $C_1$-$C_{20}$ alkyl or ether group, or an amino acid residue (D or L) as described above.

In another embodiment, the compound is according to the chemical formula:

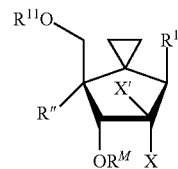

wherein:

$R^1$ is as described above, and typically cytosine, 5-methylcytosine, 5-fluorocytosine, 5-iodocytosine, uracil, thymine, 5-fluorouracil, or 5-iodouracil;

R" is H or $N_3$ (often H);

X and X' are each independently H, $C_1$-$C_4$ alkyl (often $CH_3$), $OR^{MA}$, or a halogen (often F or Cl, more often F);

$R^{11}$ is H, an acyl group, a $C_1$-$C_{20}$ alkyl or ether group or an amino acid residue (D or L), a peptide residue, a lipid (including phospholipid), cholesterol or cholesterol derivative, a carbohydrate, phosphate, diphosphate, triphosphate, phosphodiester, or phosphoramidate group, or together, $R^1$ and the hydroxyl group at the 3' position of the sugar moiety form a carbodiester, phosphodiester, or phosphoramidate group with the oxygen atoms to which they are bonded;

$R^{MA}$ is H, a $C_1$-$C_4$ alkyl group (if alkyl, often $CH_3$), an acyl group (often, a $C_2$-$C_{21}$ optionally substituted acyl group), an amino acid residue (D or L), or together with the oxygen atom to which $R^M$ is attached forms a carbodiester, phosphodiester, or phosphoramidate group with the oxygen atom to which $R^{MA}$ is attached; and, $R^M$ is H, a $C_1$-$C_4$ alkyl group (if alkyl, often $CH_3$), an acyl group (often, a $C_2$-$C_{21}$ optionally substituted acyl group), an amino acid residue (D or L), or together with the oxygen atom to which $R^{MA}$ or $R^{11}$ is attached forms a carbodiester, phosphodiester, or phosphoramidate group with the oxygen atom to which $R^M$ is attached, or its pharmaceutically acceptable salt.

In another embodiment, the compound is according to the chemical formula:

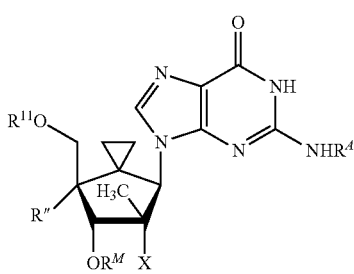

wherein:

R" is H or $N_3$ (often H);

X is H, $OR^{MA}$, or a halogen (often F);

$R^A$ is H, an acyl group, an alkyl or ether group, or an amino acid residue (D or L);

$R^{11}$ is H, an acyl group, an alkyl or ether group, or an amino acid residue (D or L), a peptide residue, a lipid (including phospholipid), cholesterol or cholesterol derivative, a carbohydrate, phosphate, diphosphate, triphosphate, phosphodiester or phosphoramidate group, or together with the oxygen to which $R^M$ is attached form a carbodiester, phosphodiester, or phosphoramidate group with the oxygen to which $R^{11}$ is attached;

$R^{MA}$ is H, a $C_1$-$C_4$ alkyl group (if alkyl, often $CH_3$), an acyl group (often, a $C_2$-$C_{21}$ optionally substituted acyl group), an amino acid residue (D or L), or together with the oxygen atom to which $R^M$ is attached forms a carbodiester, phosphodiester, or phosphoramidate group with the oxygen atom to which $R^{MA}$ is attached; and $R^M$ is H, a $C_1$-$C_4$ alkyl group (if alkyl, often $CH_3$), an acyl group (often, a $C_2$-$C_{21}$ optionally substituted acyl group), an amino acid residue (D or L), or together with the oxygen atom to which $R^{MA}$ or $R^{11}$ is attached forms a carbodiester, phosphodiester, or phosphoramidate group with the oxygen atom to which $R^M$ is attached, or a pharmaceutically acceptable salt thereof. Often $R^{MA}$ and $R^M$ are both H.

In another embodiment, the compound is according to the formula:

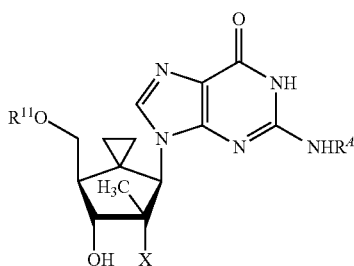

wherein X is OH or F;

$R^A$ is H, an acyl group, a $C_1$-$C_{20}$ alkyl or ether group or an amino acid residue (D or L) ($R^A$ $R^{11}$ is H, an acyl group, a $C_1$-$C_{20}$ alkyl or ether group, or an amino acid residue (D or L), a peptide residue, a lipid (including phospholipid), cholesterol or cholesterol derivative, a carbohydrate, phosphate, diphosphate, triphosphate, phosphodiester, or phosphoramidate group, or $R^{11}$ and the hydroxyl group at the 3'-position of the sugar together form a carbodiester, phosphodiester, or phosphoramidate group with the oxygen atoms to which they are bonded, or a pharmaceutically acceptable salt thereof.

In another embodiment, the compound is according to the formula:

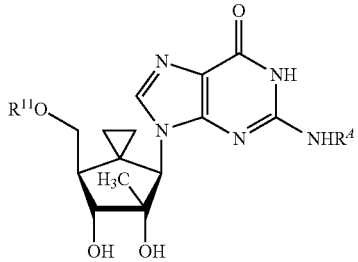

wherein:

$R^A$ is H, an acyl group, a $C_1$-$C_{20}$ alkyl or ether group, or an amino acid residue (D or L); and $R^{11}$ is H, an acyl group, a $C_1$-$C_{20}$ alkyl or ether group, or an amino acid residue (D or L), a peptide residue, a lipid (including phospholipid), cholesterol or cholesterol derivative, a carbohydrate, phosphate, diphosphate, triphosphate, phosphodiester, or phosphoramidate group, or a pharmaceutically acceptable salt thereof.

In still another embodiment, the compound is according to the chemical structure:

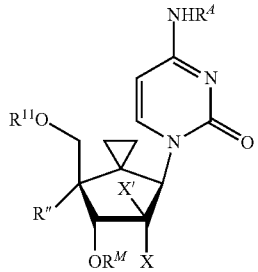

wherein:

R" is H or $N_3$;

X is $OR^{MA}$ or a halogen (often F or Cl, more often F);

X' is H or a $C_1$-$C_4$ alkyl group (often $CH_3$);

$R^A$ is H, an acyl group, a $C_1$-$C_{20}$ alkyl or ether group, or an amino acid residue (D or L) ($R^A$ is often H);

$R^{11}$ is H, an acyl group, a $C_1$-$C_{20}$ alkyl or ether group, or an amino acid residue (D or L), a peptide residue, a lipid (including phospholipid), cholesterol or cholesterol derivative, a carbohydrate, phosphate, diphosphate, triphosphate, phosphodiester, or phosphoramidate group, or $R^{11}$ and $R^M$ together form a carbodiester, phosphodiester, or phosphoramidate group with the oxygen atoms to which they are bonded;

$R^{MA}$ is H, a $C_1$-$C_4$ alkyl group (if alkyl, often $CH_3$), an acyl group (often, a $C_2$-$C_{21}$ optionally substituted acyl group, more often a $C_2$-$C_{10}$ acyl group), an amino acid residue (D or L), or together with $R^M$ forms a carbodiester, phosphodiester, or phosphoramidate group with the oxygen atoms to which $R^M$ and $R^{MA}$ are attached; and, $R^M$ is H, a $C_1$-$C_4$ alkyl group (if alkyl, often $CH_3$), an acyl group (often, a $C_2$-$C_{21}$ optionally substituted acyl group), an amino acid residue (D or L), or together with $R^{MA}$ or $R^{11}$ forms a carbodiester, phosphodiester, or phosphoramidate group with the oxygen atom to which $R^M$ and $R^{MA}$ or $R^{11}$ is attached, or a pharmaceutically acceptable salt or epimer thereof. Often $R^{MA}$ and $R^M$ are both H.

In another embodiment, the compound is according to the formula:

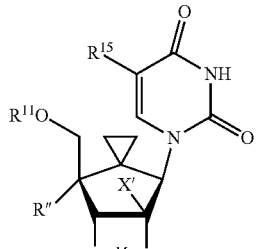

wherein:

R" is H or $N_3$ (often H);

X is $OR^{MA}$ or a halogen (often F or Cl, more often F);

X' is H, a $C_1$-$C_4$ alkyl group (often $CH_3$);

$R^{15}$ is H, F, I, or a C1-C4 alkyl group, including a $CF_3$ group;

$R^{11}$ is H, an acyl group, a $C_1$-$C_{20}$ alkyl or ether group, or an amino acid residue (D or L), a peptide residue, a lipid (including phospholipid), cholesterol or cholesterol derivative, a carbohydrate, phosphate, diphosphate, triphosphate, phosphodiester or phosphoramidate group, or together $R^{11}$ and $R^M$ form a carbodiester, phosphodiester, or phosphoramidate group with the oxygen atoms to which they are bonded;

$R^{MA}$ is H, a $C_1$-$C_4$ alkyl group (if alkyl, often $CH_3$), an acyl group (often, a $C_2$-$C_{21}$ optionally substituted acyl group, more often a $C_2$-$C_{10}$ acyl group), an amino acid residue (D or L), or together with $R^M$ forms a carbodiester, phosphodiester, or phosphoramidate group, with the oxygen atoms to which $R^M$ and $R^{MA}$ are attached; and, $R^M$ is H, a $C_1$-$C_4$ alkyl group (if alkyl, often $CH_3$), an acyl group (often, a $C_2$-$C_{21}$ optionally substituted acyl group), an amino acid residue (D or L), or together with $R^{MA}$ or $R^{11}$ forms a carbodiester, phosphodiester, or phosphoramidate group with the oxygen atom to which $R^M$ and $R^{MA}$ or $R^{11}$ is attached, or a pharmaceutically acceptable salt thereof. Often $R^{MA}$ and $R^M$ are both H.

In particular embodiments, (i) in Formula I, $R^1$ is purine or pyrimidine; $R^2$ is $CH_3$ (or wherein any of the H of $CH_3$ are replaced with F, including $CF_3$); $R^3$ is OH or F; $R^4$ is OH; and $R^5$ is H, phosphate (mono, di or tri), or phosphoramidate;

(ii) in Formula I, $R^1$ is cytosine, 5-halocytosine (for example, 5-fluorocytosine), uracil, 5-halouracil (for example, 5-fluorouracil) or thymine; $R^2$ is $CH_3$ (or wherein any of the H of $CH_3$ are replaced with F, including $CF_3$); $R^3$ is OH or F; $R^4$ is OH; and $R^5$ is H, phosphate (mono, di or tri), or phosphoramidate;

(iii) in Formula I, $R^1$ is adenine, guanine, xanthine, or hypoxanthine; $R^2$ is $CH_3$ (or wherein any of the H of $CH_3$ are replaced with F, including $CF_3$); $R^3$ is OH or F; $R^4$ is OH; and $R^5$ is H, phosphate (mono, di or tri), or phosphoramidate;

(iv) in Formula I, $R^1$ is uridine or cytosine; $R^2$ is $CH_3$; $R^3$ is OH; $R^4$ is OH; and $R^5$ is H, phosphate (mono, di or tri), or phosphoramidate;

(v) in Formula I, $R^1$ is uridine or cytosine; $R^2$ is $CH_3$; $R^3$ is F; $R^4$ is OH; and $R^5$ is H, phosphate (mono, di or tri), or phosphoramidate;

(vi) in Formula I, $R^1$ is uridine or cytosine; $R^2$ is H; $R^3$ is F; $R^4$ is OH; and $R^5$ is H, phosphate (mono, di or tri), or phosphoramidate;

(vii) in Formula I, $R^1$ is 5-fluorouridine or 5-fluorocytosine; $R^2$ is $CH_3$; $R^3$ is OH; $R^4$ is OH; and $R^5$ is H, phosphate (mono, di or tri), or phosphoramidate;

(viii) in Formula I, $R^1$ is 5-fluorouridine or 5-fluorocytosine; $R^2$ is $CH_3$; $R^3$ is F; $R^4$ is OH; and $R^5$ is H, phosphate (mono, di or tri), or phosphoramidate;

(ix) in Formula I, $R^1$ is 5-fluorouridine or 5-fluorocytosine; $R^2$ is H; $R^3$ is F; $R^4$ is OH; and $R^5$ is H, phosphate (mono, di or tri), or phosphoramidate;

(x) in Formula I, either $R^2$ is F and $R^3$ is H or $R^2$ is H and $R^3$ is F;

(xi) in Formula I, $R^2$ is $CH_3$ and $R^3$ is OH or F;

(xii) in Formula II, B is uridine or cytosine; $R^6$ is H; and $R^5$ is H, phosphate (mono, di or tri), or phosphoramidate;

(xiii) in Formula II, B is uridine; $R^6$ is H; and $R^5$ is phosphoramidate;

(xiv) in Formula II, B is cytosine; $R^6$ is H; and $R^5$ is phosphoramidate;

(xv) in Formula I or II, $R^5$ is phosphoramidate;

(xvi) in Formula I, $R^1$ is a non-natural heteroaryl or heterocyclic moiety;

(xvii) in Formula II, B is a non-natural heteroaryl or heterocyclic moiety;

(xviii) in Formula I, $R^2$ and $R^3$ are fluoro;

(xix) in Formula I or II, $R^5$ and $R^7$ form a bridge;

(xx) in Formula I or II, $R^5$ and $R^7$ are both amino acids; and, (xxi) in Formula I or II, $R^5$ is a phosphoramidate and $R^7$ is an amino acid or other oxygen-protecting group.

In alternative embodiments of compounds (i) through (xxi), Formula III or IV is used in place of either Formula I or II.

Since Flaviviridae are positive stranded RNA viruses, in one embodiment, an $R^1$ or B is selected which the host would mimic or be related to an RNA base, such as uracil, cytosine, guanine, or adenosine, or a base that is easily metabolized to an RNA base. In an alternative embodiment, the active spiro [2.4]heptane has an $R^1$ or B that is a derivative of an RNA base, for example, a prodrug of uracil, cytosine, guanine, or adenosine or a halogenated, alkylated, phosphorylated, or acylated derivative.

II. Definitions

The following terms are used to describe the present invention. In instances where a term is not specifically defined herein, that term is given an art-recognized meaning by those of ordinary skill applying that term in context to its use in describing the present invention.

The term "pharmaceutically acceptable salt or prodrug" is used throughout the specification to describe any pharmaceutically acceptable form (such as an ester, phosphate ester, salt of an ester, or a related group) of a spiro[2.4]heptane which, upon administration to a patient, provides the desired active compound. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including sulfate, nitrate, bicarbonate, and carbonate salts. Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium, or lithium) or alkaline earth metal (for example calcium) salts of carboxylic acids can also be made.

Pharmaceutically acceptable prodrug refers to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated, or dephosphoamidated to produce the active compound. The compounds of this invention possess antiviral activity against Flaviviridae, or are metabolized to a compound that exhibits such activity. The spiro[2.4]heptane can also be administered as a 5'-phosphoether lipid or a 5'-ether lipid, or a "SATE" derivative The term "alkyl" shall mean within its context, a linear, branch-chained, or cyclic fully saturated hydrocarbon radical or alkyl group which may be optionally substituted (for example, with halogen, including F).

The term "alkenyl" refers to a non-aromatic hydrocarbon group which contains at least one double bond between adjacent carbon atoms and a similar structure to an alkyl group as otherwise described herein. For example, a vinyl group is an alkenyl group as otherwise described herein.

The term "alkynyl" refers to a non-aromatic hydrocarbon group containing at least one triple bond between adjacent carbon atoms and a similar structure to an alkyl group as otherwise described herein.

The term "substituted" indicates that the moiety may have at least one additional substituent, including but not limited to halogen (F, Cl, Br, I), OH, methyl, $CF_3$, phenyl, benzyl, $N_3$, alkyl, alkenyl, alkynyl, etc.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present invention at any available stable position on the ring(s) or as otherwise indicated in the chemical structure presented.

A heteroaryl ring system is a saturated or unsaturated ring with one or more nitrogen, oxygen, or sulfur atoms in the ring (moncyclic) including but not limited to imidazole, furyl, pyrrole, furanyl, thiene, thiazole, pyridine, pyrimidine, pyrazine, triazole, oxazole, or fused ring systems such as indole, quinoline, etc., among others, which may be optionally substituted as described above. Heteroaryl groups include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising two or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "heterocycle" refers to a cyclic group which contains at least one heteroatom, i.e., O, N, or S, and may be aromatic (heteroaryl) or non-aromatic. Exemplary non-aromatic heterocyclic groups for use in the present invention include, for example, pyrrolidinyl, pyrrolinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimide, and succinimide, among others.

In one embodiment, the term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolo-pyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, trimethylhexylsilyl, t-butyldimethylsilyl and t-butyldiphenylsilyl, trityl, alkyl groups, and acyl groups such as acetyl and propionyl, methanesulfonyl, and p-toluenesulfonyl. Alternatively, the purine or pyrimidine base can optionally be substituted such that it forms a viable prodrug, which can be cleaved in vivo. Examples of appropriate substituents include acyl moiety, an amine or cyclopropyl (e.g., 2-amino, 2,6-diamino or cyclopropyl guanosine).

The term acyl refers to a carboxylic acid ester in which the non-carbonyl moiety of the ester group is selected from straight, branched, or cyclic alkyl or lower alkyl (i.e., $C_1$-$C_4$), alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl), or diphenylmethylsilyl. Aryl groups in the esters optimally comprise a phenyl group. The term "lower acyl" refers to an acyl group in which the non-carbonyl moiety is lower alkyl (i.e., C1-$C_4$).

The term "amino acid" or "amino acid residue" refers to a D- or L-natural or non-naturally occurring amino acid. Representative amino acids alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine, among others.

The term "oxygen-protecting group" as used herein refers to a moiety that is covalently attached to oxygen and which can be removed, and typically replaced with hydrogen, when appropriate. For example, an oxygen-protecting group may be a group that is removed in vivo after administration to a host, in vitro by a cell, or it may be removed during a manufacturing process.

Phosphate ester refers to mono, di and tri phosphates unless otherwise indicated.

The term "phosphoamidate," phosphoramidate," or "phosphoroamidate" is a moiety that has a phosphorus bound to three oxygen groups and an amine (which may optionally be substituted). The typical structure is —P(=O)(OR$^{100}$)(OR$^{110}$)NR$^{120}$R$^{130}$, where R$^{100}$, R$^{110}$, R$^{120}$, and R$^{130}$ can be H or desired organic substituents. Suitable phosphoramidates useful in the present invention are described by Madela, Karolina and McGuigan in 2012, "Progress in the development of anti-hepatitis C virus nucleoside and nucleotide prodrugs", *Future Medicinal Chemistry* 4(5), pages 625-650 10:1021/jm300074y. Additional phosphoramidates useful in the present invention are described in U.S. Pat. Nos. 7,964,580; 8,071,568; 8,148,349; 7,879,815; 7,902,202; 7,547,704; 7,951,789; 8,324,179; EP 2120565; EP 1143995; U.S. Pat.

Nos. 6,455,513; and 8,334,270. Other phosphoramidates are described in the nucleoside patents described in the Background of the Invention.

Phosphoramidate groups for use in the present invention include those of the structures:

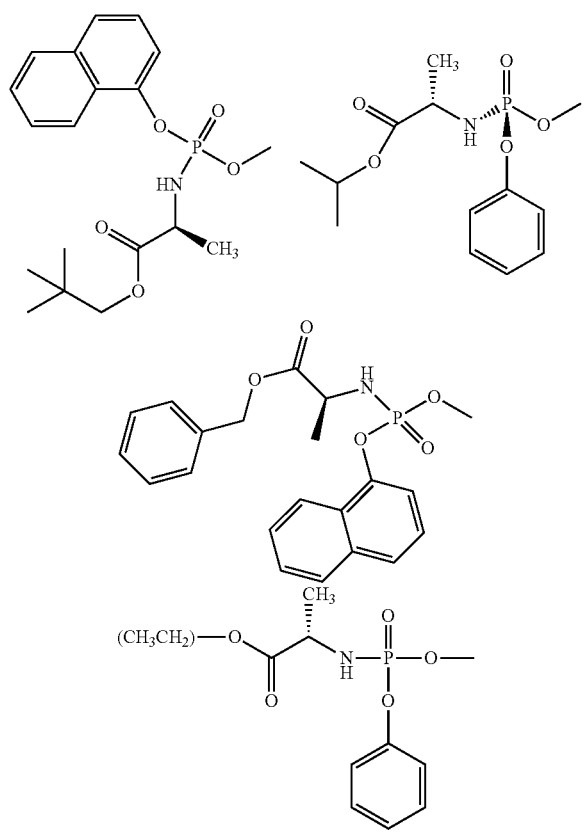

Other phosphoramidates include those of the structure:

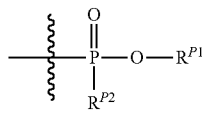

wherein:

$R^{P1}$ is an optionally substituted linear, branched, or cyclic alkyl group, or an optionally substituted aryl, heteroaryl or heterocyclic group or a linked combination thereof; and $R^{P2}$ is a —$NR^{N1}R^{N2}$ group or a B' group;

wherein:

$R^{N1}$ and $R^{N2}$ are each independently H or a alkyl group, often a $C_1$-$C_6$ alkyl group which may be optionally substituted with one, two or three hydroxyl groups, and, B' is a

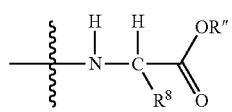

group;

wherein:

$R^8$ is sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often $R^8$ is derived from alanine, leucine, valine, isoleucine or threonine), and, R" is H or an optionally substituted $C_1$ to $C_{20}$ linear, branched, or cyclic alkyl group, or an optionally substituted aryl, heteroaryl or heterocyclic group as otherwise described herein.

Preferred $R^{P1}$ groups include optionally substituted $C_8$-$C_{20}$ alkyl groups and optionally substituted phenyl, naphthyl, and monocyclic heteroaryl groups, especially those groups (particularly lipophilic groups) which enhance bioavailability of the compounds in the skin of the patient and which exhibit reduced toxicity, enhanced therapeutic index and enhanced pharmacokinetics (the compounds are metabolized and excreted more slowly).

The term "D-configuration" as used in the context of the present invention refers to the principle configuration which mimics the natural configuration of sugar moieties as opposed to the unnatural occurring nucleosides or "L" configuration. The term "β" or "β anomer" is used with reference to nucleoside analogs in which the nucleoside base is configured (disposed) above the plane of the carbocyclic moiety in the nucleoside analog.

The terms "coadminister" and "coadministration" or combination therapy are used to describe the administration of at least one of the spiro[2.4] compounds according to the present invention in combination with at least one other anti-Flaviviridae agent, often at least one additional anti-HCV agent, including other spiro[2.4]heptane anti-HCV agents which are disclosed herein. The timing of the coadministration is best determined by the medical specialist treating the patient. It is sometimes preferred that the agents be administered at the same time. Alternatively, the drugs selected for combination therapy may be administered at different times to the patient. Of course, when more than one viral or other infection or other condition is present, the present compounds may be combined with other agents to treat that other infection or condition as required.

The term host, as used herein, refers to a unicellular or multicellular organism in which the virus can replicate, including cell lines and animals, and typically a human. Alternatively, the host can be carrying a part of the flavivirus or pestivirus genome, whose replication or function can be altered by the compounds of the present invention. The term host specifically refers to infected cells, cells transfected with all or part of the Flaviviridae, for example, HCV, genome and animals, in particular, primates (including chimpanzees) and humans. In most animal applications of the present invention, the host is a human patient. Veterinary applications, in certain indications, however, are clearly anticipated by the present invention (such as chimpanzees). A number of the Flaviviridae viruses are specific with respect to the host animal that is infected, and in those instances the term host refers to those animals, including humans infected or susceptible to infection by that Flaviviridae. The host can be for example, bovine, equine, avian, canine, feline, etc.

III. Methods of Treatment or Prophylaxis

Treatment, as used herein, refers to the administration of an active compound to a host that is infected with a Flaviviridae virus, for example, hepatitis C. The term "prophylactic" or preventative, when used, refers to the administration of an active compound to prevent or reduce the likelihood of an occurrence of the viral disorder. The present invention includes both treatment and prophylactic or preventative therapies. In one embodiment, the active compound is administered to a host who has been exposed to and thus at risk of infection by a Flaviviridae, for example, a hepatitis C infection.

The invention is directed to a method of treatment or prophylaxis of a Flaviviridae viral infection in a host in need thereof, including hepatitis C virus, Yellow Fever virus, Dengue virus, Japanese Encephalitis, and West Nile viruses, especially HCV, including drug resistant and multidrug resistant forms of HCV and related disease states, conditions, or complications of an HCV infection, including cirrhosis and related hepatotoxicities, as well as other conditions that are secondary to a Flaviviridae infection, such as weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, kidney failure, enlarged spleen, decrease in blood cells, anemia, thrombocytopenia, jaundice, and hepatocellular cancer, among others. The method comprises administering to a host in need thereof of an effective amount of at least one spiro [2.4]heptane as described herein, optionally in combination with at least one additional bioactive agent, for example, an additional anti-HCV or anti-Flaviviridae and/or anticancer agent, further in combination with a pharmaceutically acceptable carrier additive and/or excipient.

In yet another aspect, the present invention is a method for prevention or prophylaxis of a Flaviviridae infection, such as an HCV infection or a disease state or related or follow-on disease state, condition or complication of a Flaviviridae, including an HCV, infection including cirrhosis and related hepatotoxicities, weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, kidney failure, enlarged spleen, decrease in blood cells, anemia, thrombocytopenia, jaundice, and hepatocellular (liver) cancer, among others, said method comprising administering to a patient at risk with an effective amount of at least one compound according to the present invention as described above in combination with a pharmaceutically acceptable carrier, additive, or excipient, optionally in combination with another anti-HCV agent. In another embodiment, the active compounds of the invention can be administered to a patient after a hepatitis-related liver transplantation to protect the new organ.

The spiro[2.4]heptane can be administered if desired as any salt or prodrug that upon administration to the recipient is capable of providing directly or indirectly the parent compound, or that exhibits activity itself. Nonlimiting examples are the pharmaceutically acceptable salts and a compound, which has been modified at a function group, such as a hydroxyl or amine function, to modify the biological activity, pharmacokinetics, half-life, controlled delivery, lipophilicity, absorption kinetics, ease of phosphorylation to the active 5'-triphosphate or efficiency of delivery using a desired route of administration, of the compound. Methods to modify the properties of an active compound to achieve target properties are known to those of skill in the art or can easily be assessed by standard methods, for example, acylation, phosphorylation, phosphoamidation, phosphonation, alkylation, pegylation, or selecting an $R^1$ or B that is metabolized to a desired $R^1$ or B.

IV. Pharmaceutical Compositions

In an aspect of the invention, pharmaceutical compositions according to the present invention comprise an anti-Flaviviridae (especially including an anti-HCV) effective amount of at least one of the spiro[2.4]compounds described herein, optionally in combination with a pharmaceutically acceptable carrier, additive, or excipient, further optionally in combination with at least one other anti-viral, such as an anti-HCV agent.

The invention includes pharmaceutical compositions that include an effective amount to treat a Flaviviridae infection, for example, a hepatitis C infection, of one of the spiro[2.4] heptane compounds of the present invention or its salt or prodrug, in a pharmaceutically acceptable carrier or excipient. In an alternative embodiment, the invention includes pharmaceutical compositions that include an effective amount to prevent a Flaviviridae infection, for example, a hepatitis C infection, of one of the spiro[2.4]heptane compounds of the present invention or its salt or prodrug, in a pharmaceutically acceptable carrier or excipient.

One of ordinary skill in the art will recognize that a therapeutically effective amount will vary with the infection or condition to be treated, its severity, the treatment regimen to be employed, the pharmacokinetics of the agent used, as well as the patient or subject (animal or human) to be treated, and such therapeutic amount can be determined by the attending physician or specialist.

The spiro[2.4]heptane compound according to the present invention can be formulated in admixture with a pharmaceutically acceptable carrier. In general, it is preferable to administer the pharmaceutical composition in orally-administrable form, but certain formulations may be administered via a parenteral, intravenous, intramuscular, topical, transdermal, buccal, subcutaneous, suppository, or other route, including intranasal spray. Intravenous and intramuscular formulations are often administered in sterile saline. One of ordinary skill in the art may modify the formulations to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other), and ether (alkyl and related) derivatives, phosphate esters, phosphoramidates, and various salt forms of the present compounds, are preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

The amount of compound included within therapeutically active formulations according to the present invention is an effective amount for treating the Flaviviridae infection or condition, for example an HCV infection, reducing the likelihood of a HCV infection or the inhibition, reduction, and/or abolition of HCV or its secondary effects, including disease states, conditions, and/or complications which occur secondary to HCV. In general, a therapeutically effective amount of the present compound in pharmaceutical dosage form usually ranges from about 0.001 mg/kg to about 100 mg/kg per day or more, more often, slightly less than about 0.1 mg/kg to more than about 25 mg/kg per day of the patient or considerably more, depending upon the compound used, the condition or infection treated and the route of administration. The active nucleoside compound according to the present invention is often administered in amounts ranging from about 0.1 mg/kg to about 15 mg/kg per day of the patient, depending upon the pharmacokinetics of the agent in the patient. This dosage range generally produces effective blood level concentrations of active compound which may range from about 0.001 to about 100, about 0.05 to about 100 micrograms/cc of blood in the patient.

Often, to treat, prevent or delay the onset of these infections and/or to reduce the likelihood of a Flaviviridae infection, for example, an HCV infection, or a secondary disease state, condition or complication of HCV, the compositions will be administered in oral dosage form in amounts ranging from about 250 micrograms up to about 500 mg or more at least once a day, for example, at least 25, 50, 100, 150, 250 or 500 milligrams, up to four times a day. The present compounds are often administered orally, but may be administered parenterally, topically, or in suppository form, as well as intranasally, as a nasal spray or as otherwise described herein.

In the case of the co-administration of the present compounds in combination with another anti-HCV or Flaviviridae compound as otherwise described herein, the amount of the compound according to the present invention to be administered ranges from about 0.01 mg/kg of the patient to about 500 mg/kg. or more of the patient or considerably more, depending upon the second agent to be co-administered and its potency against the virus, the condition of the patient and severity of the disease or infection to be treated and the route of administration. The other anti-HCV or anti-Flaviviridae agent may for example be administered in amounts ranging from about 0.01 mg/kg to about 500 mg/kg. In certain preferred embodiments, these compounds may be often administered in an amount ranging from about 0.5 mg/kg to about 50 mg/kg or more (usually up to about 100 mg/kg), generally depending upon the pharmacokinetics of the two agents in the patient. These dosage ranges generally produce effective blood level concentrations of active compound in the patient.

For purposes of the present invention, a prophylactically or preventive effective amount of the compositions according to the present invention falls within the same concentration range as set forth above for therapeutically effective amount and is usually the same as a therapeutically effective amount.

Administration of the active compound may range from continuous (intravenous drip) to several oral or intranasal administrations per day (for example, Q.I.D.) or transdermal administration and may include oral, topical, parenteral, intramuscular, intravenous, sub-cutaneous, transdermal (which may include a penetration enhancement agent), buccal, and suppository administration, among other routes of administration. Enteric coated oral tablets may also be used to enhance bioavailability of the compounds from an oral route of administration. The most effective dosage form will depend upon the bioavailability/pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is often intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs, and solutions, suitable carriers and additives including water, glycols, oils, alcohols, flavoring agents, preservatives, coloring agents, and the like may be used. For solid oral preparations such as powders, tablets, capsules, and for solid preparations such as suppositories, suitable carriers and additives including starches, sugar carriers, such as dextrose, manifold, lactose, and related carriers, diluents, granulating agents, lubricants, binders, disintegrating agents, and the like may be used. If desired, the tablets or capsules may be enteric-coated or sustained release by standard techniques. The use of these dosage forms may significantly enhance the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents, and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In particularly preferred embodiments according to the present invention, the compounds and compositions are used to treat, prevent or delay a HCV infection or a secondary disease state, condition or complication of HCV.

IV. Combination and Alternation Therapy

It is well recognized that drug-resistant variants of viruses can emerge after prolonged treatment with an antiviral agent. Drug resistance most typically occurs by mutation of a gene that encodes for an enzyme used in viral replication. The efficacy of a drug against a Flaviviridae infection, including an HCV infection, can be prolonged, augmented, or restored by administering the compound in combination or alternation with another, and perhaps even two or three other, antiviral compounds that induce a different mutation or act through a different pathway, from that of the principle drug. Alternatively, the pharmacokinetics, bio distribution, half-life, or other parameter of the drug can be altered by such combination therapy (which may include alternation therapy if considered concerted). Since the disclosed spiro[2.4]heptanes are NS5B polymerase inhibitors, it may be useful to administer the compound to a host in combination with, for example a:

(1) Protease inhibitor, such as an NS3/4A protease inhibitor;
(2) NS5A inhibitor;
(3) Another NS5B polymerase inhibitor;
(4) NS5B non-substrate inhibitor;
(5) Interferon alfa-2a, which may be pegylated or otherwise modified, and/or ribavirin;
(6) Non-substrate-based inhibitor;
(7) Helicase inhibitor;
(8) Antisense oligodeoxynucleotide (S-ODN);

(9) Aptamer;
(10) Nuclease-resistant ribozyme;
(11) iRNA, including microRNA and SiRNA;
(12) Antibody, partial antibody or domain antibody to the virus, or
(13) Viral antigen or partial antigen that induces a host antibody response.

Non limiting examples of anti-HCV agents that can be administered in combination with the spiro[2.4]heptanes of the invention are:
  (i) protease inhibitors such as telaprevir (Incivek), boceprevir (Victrelis), ACH-2684; AZD-7295; BMS-791325; danoprevir; Filibuvir; GS-9256; GS-9451; MK-5172; Setrobuvir; Sovaprevir; Tegobuvir; VX-135; VX-222 and ALS-220;
  (ii) NS5A inhibitor such as ACH-2928 and ACH-3102;
  (iii) NS5B inhibitors such as ACH-3102; AZD-7295; Clemizole; ITX-5061; PPI-461; PPI-688; IDX-719, PSI-7977 and mericitabine;
  (iv) NS5B inhibitors such as MBX-700; and,
  (v) Antibody such as GS-6624.

If the spiro[2.4]heptane is administered to treat advanced hepatitis C leading to liver cancer or cirrhosis, in one embodiment, the compound can be administered in combination or alternation with another drug that is typically used to treat hepatocellular carcinoma (HCC), for example, as described by Andrew Zhu in "New Agents on the Horizon in Hepatocellular Carcinoma" Therapeutic Advances in Medical Oncology, V 5(1), January 2013, 41-50. Examples of suitable compounds for combination therapy where the host has or is at risk of HCC include anti-angiogenic agents, sunitinib, brivanib, linifanib, ramcirumab, bavcizumab, cediranib, pazopanib, TSU-68, lenvatinib, antibodies against EGFR, mTor inhibitors, MEK inhibitors, and histone decetylace inhibitors.

V. Process of Preparation of Spiro[2.4]heptanes of the Invention

General methods for providing the compounds of the present invention are known in the art or described herein. Examples of processes to prepare the described compounds are set out in detail in FIGS. 2-11 (with details of reagents provided in the Brief Description of the Figures) which can be used as desired or with minor modification within the routineer's skill. Further exemplification is provided below in the detailed synthetic examples.

The following abbreviations are used in the synthetic schemes.
  (Boc)$_2$O: Di-tert-butyl dicarbonate;
  DMAP: 4-Dimethylaminopyridine;
  THF: Tetrahydrofuran (THF), anhydrous;
  OsO$_4$: Osmium tetraoxide;
  NMO: N-Methylmorpholine N-oxide;
  BzCl: Benzoyl Chloride;
  NaBH$_4$: Sodium borohydride;
  HCl: Hydrochloric Acid;
  NaNO$_2$: Sodium Nitrite;
  CH$_3$COOH: Acetic Acid;
  NaOMe: Sodium Methoxide;
  PTSA: p-toluene sulphonic acid;
  TBDMSCl$_2$: 1,3-Dichloro-1,1,3,3-tetraisopropyldisiloxane;
  DCM: Methylene chloride (CH$_2$Cl$_2$), anhydrous;
  m-CPBA: m-Chloro perbenzoic acid;
  n-BuLi: n-Butyl Lithium;
  CeCl$_3$.7H$_2$O: Cerium(III)chloride heptahydrate;
  MeI$_2$: Diido methane;
  DIAD: Diisopropyl azodicarboxlate;
  TPP: Triphenylphosphine;
  TFA: Trifluoro acetic acid;
  TBAF: Tetrabutylammonium fluoride;
  NMI: N-methyl Imidazole;
  DPPA: Diphenylphosphoryl azide;
  NaH: Sodium hydride;
  EtOAc: Ethyl acetate;
  Silica gel (230 to 400 mesh, Sorbent);
  Na$_2$SO$_4$: Sodium Sulphate (anhydrous);
  DMF: N'N Dimethyl formamide, androus;
  NH$_4$OH: Ammoinum hydroxide;
  EtOH: Ethanol;
  MeOH: Methanol;
  DAST: Diethylaminosulfur trifluride;
  NaHCO$_3$: Sodium bicarbonate;
  BnCl: Benzyl Chloride;
  NH$_3$: Ammonia;
  PCC: Pyridinium chlorochromate;
  CH$_3$Li: Methyl lithium; and,
  CH$_3$MgBr: Methyl magnesium bromide.

EXAMPLES

General Methods

Melting points were determined on a MeI-temp II laboratory device and are uncorrected. Nuclear magnetic spectra were recorded on Varian Mercury 400 spectrometer at 400 MHz for $^1$H NMR and 100 MHz for $^{13}$C NMR or Varian Inova 500 spectrometer at 500 MHz for $^1$H NMR and 125 MHz for $^{13}$C NMR with tetramethylsilane as an internal standard. Chemical shifts ($\delta$) are quoted as s (singlet), bs (broad singlet), d (doublet), t (triplet), q (quartet), m (multiplet). U.V spectra were recorded on a Beckman DU-650 spectrophotometer. Optical rotations were measured on JASCO DIP-370 digital polarimeter. High resolution mass spectra were recorded on a Micromass Autospec high-resolution mass spectrometer. Elemental analyses were performed by Atlantic Microlabs Inc. Norcross, Ga. TLC was performed on Uni-plates (Silica Gel) purchased from Analtech Co.

Figure 2:
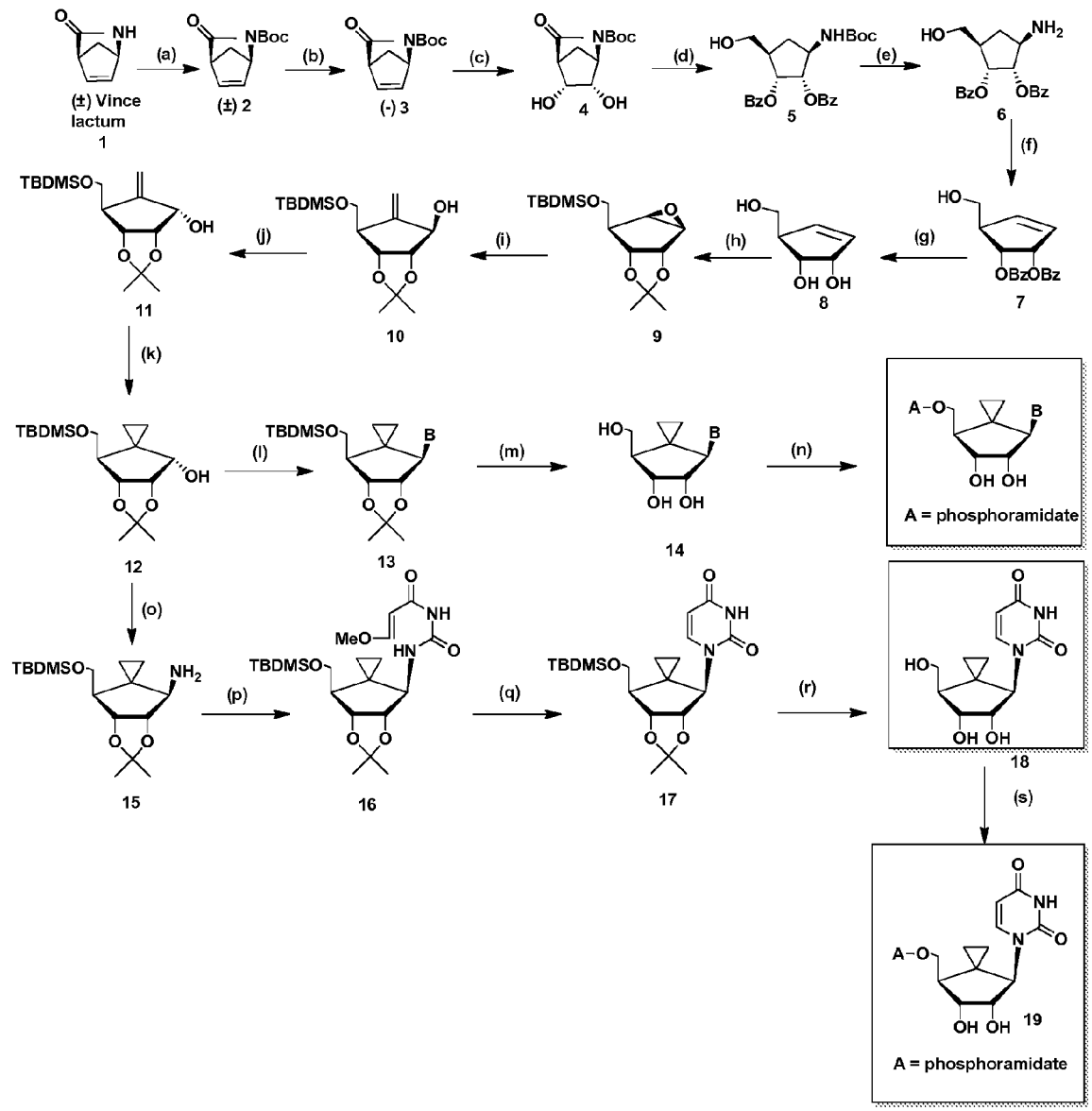
FIGS. 2-11 provide various processes for the preparation of the spiro[2.4] compounds of the invention.

Detailed Synthetic Protocols for FIG. 2

[(±)-tert-butyl 3-oxo-2-azabicyclo(2.2.1)hept-5-ene-2-carboxylate] (2). A solution of di-tert-butyl dicarbonate (110.0 g, 504.5 mmol) in tetrahydrofuran (50 ml) was added slowly to a suspension of racemic 1 (50.0 g, 403.2 mmol), and 4-dimethylaminopyridine (0.5 g, 4.0 mmol) in tetrahydrofuran (150 ml). The brown, hazy solution was stirred at 20° C. until reaction was complete. The solution was concentrated in vacuo to give brown foam. Recrystallisation twice from cyclohexane afforded the product 2 (racemic) as pale pink crystals (80.8 g, 80%); mp 70.5-71.5° C.; $^1$H NMR (CDCl$_3$): $\delta$ 1.5 (s, 5H), 2.15 (d, J=8.5 Hz, 1H), 2.35 (d, J=8.5 Hz, 1H), 3.39 (s, 1H), 4.96 (s, 1H), 6.66 (m, 1H), 6.89 (dd, J=5.6 & 2.1 Hz, 1H); MS: (M+H)$^+$ 210.

(−)-[(1R,4S)-tert-butyl 3-oxo-2-azabicyclo(2.2.1)hept-5-ene-2-carboxylate] (3). Savinase (15 ml, 16 L) was added to a solution (500 ml) containing 10 g (47.8 mmol) of (±)2 in 50% tetrahydrofuran: 50% phosphate buffer (50 mM, pH 8.0) at 30° C. The reaction was monitored by TLC for up to 2 days. Upon completion of the reaction (51% conversion), the pH of the clarified solution was raised to 9 with a sodium bicarbonate solution. This was then extracted with cyclohexane (200 mL×2). The combined organic phase was back extracted with 100 ml of sodium bicarbonate solution and subsequently washed with 100 ml of brine. Evaporation and drying yielded brown crude. The obtain crude was purified by the column chromatography elutent 20% EtOAc/hexane gave free flowing white solid (−)-3 (4.2 g, 84%) which was identified by 1H NMR and by with an authentic enantiomerically pure standard (optical rotation of standard $[\alpha]^{24}_D$ −194° (c 2.0, CHCl$_3$). The enantiomeric excess was better than 99% as analyzed by the optical rotation. Mp 88.6° C.; $[\alpha]^{24}_D$ −193° (c 2.0, CHCl$_3$); $^1$H NMR (CDCl$_3$): δ 1.5 (s, 5H), 2.15 (d, J=8.5 Hz, 1H), 2.35 (d, J=8.5 Hz, 1H), 3.39 (s, 1H), 4.96 (s, 1H), 6.66 (m, 1H), 6.89 (dd, J=5.6 & 2.1 Hz 1H).

(−)-(1R,4S,5R,6S)-tert-butyl-5,6-dihydroxy-3-oxo-2-azabicyclo[2.2.1]heptane-2-carbo-late (4). To a solution of tert-butyl 3-oxo-2-azabicyclo (2.2.1) hept-5-ene-2-carboxylate 3 (50.0 g, 239.2 mmol) in acetone (200 mL), N-Methylmorpholine N-oxide (55.9 g, 477.7 mmol) was added at 0° C. with stirring followed by a solution of OsO$_4$ (121 mg, 0.476 mmol) in tert-butyl alcohol (2.5 mL), and the mixture was stirred at room temperature for 2 hr. Solvents were evaporated in vacuo, and the residue was purified by flash column chromatography on silica gel using 30% EtOH/hexane as the eluent to give a white solid (35 g, 70%). $[\alpha]^{24}_D$ −28.19 (c 1.0 CHCl$_3$); $^1$H-NMR (500 MHz, CDCl$_3$): δ 4.33 (m, 1H), 4.24 (m, 1H), 4.09 (m, 1H), 3.92 (brs, 1H), 3.76 (brs, 1H), 2.80 (m, 1H), 2.10 (d, J=10.5 Hz, 1H), 1.99 (d, J=10.5 Hz, 1H), 1.52 (s, 9H); HR-MS Calcd. For (C$_{11}$H$_{17}$NO$_5$+H)$^+$ 244.1107, found 244.1321.

(−)-(1R,2S,3R,5R)-3-((tert-butoxycarbonyl)amino)-5-(hydroxymethyl)cyclopentane-1,2-diyl dibenzoate (5). Benzoyl chloride (11.9 mL, 102.8 mmol) was added into a solution of diol 4 (10.0 g, 41.1 mmol) and DMAP (7.5 g, 61.4 mmol) in anhydrous dichloromethane (150 ml) at 0° C. The mixture was then stirred for 1 hr, quenched with water and the mixture was extracted with DCM (50 mL×2). The combined organic layers were washed with brine (150 mL) dried over Na$_2$SO$_4$. The solvent was removed and the residue was purified by silica gel column chromatography (8% EtOAc/hexane) to give benzoylated intermediate as white solid. $[\alpha]^{24}_D$ −43.40; $^1$H-NMR (500 MHz, CDCl$_3$): δ 7.82 (m, 4H), 7.50 (m, 2H), 7.25 (m, 4H), 5.59 (d, J=5.5 Hz, 1H), 5.48 (d, J=5.5 Hz, 1H), 4.70 (m, 1H), 3.13 (m, 1H), 2.43 (d, J=10.5 Hz, 1H), 2.76 (d, J=10.5 Hz, 1H), 1.57 (s, 9H). The bezoylated intermediated (12.0 g, 26.6 mmol) dissolved in the Methanol and added sodium borohydried (2.7 g, 66.5 mmol) at 0° C. The reaction was allowed to warm to room temperature. After 1.5 hr mixture was quenched with 1 N HCl and concentrated in vacuo. The aqueous layer was extracted with ethyl acetate (100 mL×2) and combine organic layers were washed with water dried over Na$_2$SO$_4$ and concentrated in reduced pressure. The residue was purified by silica gel column chromatography (50% DCM/hexane) to give compound 5 (8.5 g, 95%) as off white solid. mp 78-79° C.; $^1$H-NMR (500 MHz, CDCl$_3$): δ 7.97 (m, 4H), 7.54 (m, 2H), 7.38 (m, 4H), 5.56 (m, 1H), 5.38 (s, 1H), 5.30 (m, 1H), 4.52 (m, 1H), 3.87 (m, 1H), 3.72 (m, 1H), 2.52 (m, 2H), 1.43 (s, 9H); HR-MS Calcd. For (C$_{25}$H$_{29}$NO$_7$+H)$^+$ 456.1944, found 456.2017.

(−)-(1R,2S,3R,5R)-3-amino-5-(hydroxymethyl)cyclopentane-1,2-diyl dibenzoate hydrochloride (6). 2 N solution of HCl in ether (15 ml) was added in stirring solution of compound 5 (10.0 g, 21.9 mmol) in methanol at 0° C. The mixture was allowed to warm to room temperature gradually and continue stirred for 2 hr. Solvent was evaporated under reduced pressure, and the residue was treated with anhydrous ether (120 mL) to precipitate the product 6. The precipitated product was washed with ether (50 mL×2) afforded the titled compound as white solid. $[\alpha]^D_{25}$ −28.19°; $^1$H NMR (500 MHz, DMSO-d$_6$): δ 8.40 (bs, 2H, D$_2$O exchange, NH$_2$), 7.88 (m, 4H), 7.64 (m, 2H), 7.45 (m, 4H), 5.48 (m, 2H), 5.07 (m, 1H), 3.96 (m, 1H), 3.61 (m, 1H), 3.52 (m, 1H), 2.47 and 2.39 (m, 1H), 1.63 (m, 1H). HR-MS Calcd. For (C$_{20}$H$_{21}$NO$_5$)$^+$ 355.1420, found 335.1293.

(+)-(1R,2S,5R)-5-(hydroxymethyl)cyclopent-3-ene-1,2-diyl dibenzoate (7). To a well stirred solution of (−)-(1R,2S,3R,5R)-3-amino-5-(hydroxymethyl)cyclopentane-1,2-diyl dibenzoate hydrochloride (6) (10.0 g, 25.5 mmol) in mixture of acetonitrile/water (1:1) was added sodium nitrite (8.8 g, 127.8 mmol) by portion wise at 0° C. After 15 minutes 50% aqueous acetic acid solution was added drop wise over a period of 0.5 hr and the mixture was vigorously stirred for 2 hr. The organic solvent was removed under reduced pressure and the rest of mixture was quenched with water. The aqueous phase was extracted with EtOAc (50 mL×3). The combined organic layers were dried over Na$_2$SO$_4$, filtered and the solvent was removed under reduced pressure. The residue was purified by flash silica gel column chromatography (20% EtOAc/hexane) to give compound 7. $[\alpha]^{24}_D$ −156° (c 1.0, CHCl$_3$); $^1$H NMR (500 MHz, DMSO-d$_6$): δ 8.05 (m, 2H), 7.89 (m, 2H), 7.52 (m, 2H), 7.38 (m, 2H), 7.28 (m, 2H), 6.11 (m, 3H), 5.54 (m, 1H), 3.87-3.82 (m, 2H), 3.27 (m, 1H), 2.29 (m, 1H). HR-MS Calcd. For (C$_{25}$H$_{29}$NO$_7$+H)$^+$ 339.1154, found 339.1286.

(+)-(1R,2S,5R)-5-(hydroxymethyl)cyclopent-3-ene-1,2-diol (8). To a stirred solution of (1R,2S,5R)-5-(hydroxymethyl)cyclopent-3-ene-1,2-diyl dibenzoate (7) (7.5 g, 22.1 mmol) in methanol at room temperature under N$_2$ atmosphere was added drop wise sodium methoxide (25% by wt in methanol) (14.3 mL, 77.66 mmol) over a period of 20 minutes. The mixture was stirred at room temperature for 2 hr and quenched drop wise with 1N HCl solution to the pH neutral. The solvent was removed under reduced pressure and the obtained residue was purified by silica gel column chromatography (5% MeOH/DCM) to give triol 8 (2 g, 71%) as an oil; $[\alpha]^{24}_D$ +254.04° (c 1.0, MeOH); $^1$H NMR (500 MHz, CD$_3$OD) δ 2.78 (d, J=5.0 Hz, 1H), 3.73 (dd, J=5.0, 11.0 Hz, 1H), 3.55 (dd, J=6.5, 10.5 Hz, 1H), 3.93 (t, 1H), 4.50 (t, 1H), 5.88-5.87 (m, 1H), 5.97 (d, J=6.0 Hz, 1H); $^{13}$C NMR (125 MHz, CD$_3$OD) δ 53.7, 62.2, 73.2, 74.5, 132.0, 135.0; HR-MS Calcd. For (C$_6$H$_{10}$O$_3$−H)$^+$ 129.0630, found 129.0553.

(+)-tert-butyl(((3aR,4R,6aS)-2,2-dimethyl-4,6a-dihydro-3aH-cyclopenta[d][1,3]dioxol-4-yl)methoxy)dimethylsilane (9). To a stirred mixture of compound (8) (4.0 g, 30.7 mmol) in dry acetone (30 mL), cooled at 0° C. was added PTSA (0.18 g, 0.92 mmol) and 2,2-dimethoxy propane drop wise (4.5 mL, 36.9 mmol). The mixture was stirred at room temperature for 2 hr, quenched with solid NaHCO$_3$ (0.15 g, 1.84 mmol) and the suspension was filtered through celite pad. The celite bed was washed with acetone (20 mL) and filtrate was concentrated under vacuum. The crude acetonide was purified by silica gel column chromatography (10% EtOAc/Hexane) to give acetonide intermediate (4.0 g, 76%) as an oil. $^1$H NMR (500 MHz, CDCl$_3$) δ 5.94-5.93 (m, 1H), 5.78-5.76 (m, 1H), 5.16-5.15 (m, 1H), 4.61-4.60 (m, 1H), 3.76-3.73 (m, 1H), 3.58-3.55 (m, 1H), 3.00-2.99 (m, 1H), 1.95 (br, OH), 1.43 (s, 3H), 1.36 (s, 3H). A stirred solution of acetonide intermediate (4.0 g, 23.5 mmol) and imidazole (4.8 g, 70.5 mmol) in dry dichloromethane (50 mL) was cooled at 0° C. TBDMSCl (7.09 g, 47.0 mmol) was added in mixture and continue stirred overnight at room temperature under nitrogen atmosphere. The mixture was diluted with 100 mL dichloromethane and washed with a saturated solution of NH$_4$Cl (50 ml×2), finally with water (50 ml). The organic layer was dried over Na$_2$SO$_4$ and concentrated under reduced pressure. The residue was purified by silica gel column chromatography to give 9 as an oil (5.3 g, 80%); $[\alpha]^{24}_D$ +86.39° (c 0.2, CHCl$_3$); $^1$H NMR (500 MHz, CDCl$_3$) δ 5.83-5.81 (m, 1H), 5.73-5.71 (m, 1H), 5.09-5.07 (m, 1H), 4.51-4.49 (m, 1H), 3.67-3.65 (m, 1H,), 3.55-3.52 (m, 1H), 2.99-2.91 (m, 1H), 1.39 (s, 3H), 1.33

(s, 3H), 0.89-0.85 (m, 9H), 0.082-0.014 (m, 6H). HR-MS Calcd. For $(C_{26}H_{32}O_5Si+H)^+$ 453.2019, found 453.2123.

(+)-tert-butyl(((1aR,1bR,4aR,5S,5aR)-3,3-dimethyltetrahydro-1aH-oxireno[2',3':3,4]-cyclopenta[1,2-d][1,3]dioxol-5-yl)methoxy)dimethylsilane (10). To a stirred solution of compound 9 (5.0 g, 17.5 mmol) in dichloromethane (40 mL) at room temperature was added portion wise m-CPBA (13.6 g, 78.9 mmol). Mixture was stirred at room temperature for 6 h, quenched with saturated $NaHCO_3$ solution and the mixture was extracted with DCM (50 mL×2). The combined organic layers were washed with brine (40 mL×2) dried over $Na_2SO_4$. The solvent was removed under reduced pressure and residue was purified by silica gel column chromatography (3% EtOAc/Hexane) to give epoxide 10 (3.5 g, 66%) as an oil. $[\alpha]^{24}_D$ +58.19° (c 1.0, $CHCl_3$); $^1$H NMR (500 MHz, $CDCl_3$) δ 4.54-4.52 (m, 1H), 3.91-3.90 (m, 1H,), 3.73-3.69 (m, 1H), 3.59-3.55 (m, 3H), 2.316-2.311 (m, 1H), 1.38 (s, 3H), 1.22 (s, 3H), 0.83-0.82 (m, 9H), 0.006-0.000 (m, 6H); HR-MS Calcd. For $(C_{15}H_{28}O_4Si+H)^+$ 301.1757, found 301.1895.

(−)-(3aS,4R,6R,6aR)-6-(((tert-butyldimethylsilyl)oxy)methyl)-2,2-dimethyl-5-methylenetetrahydro-3aH-cyclopenta[d][1,3]dioxol-4-ol (11). To a −10° C. suspension of trimethylsulfonium iodide (30 g, 149.5 mmol) in THF (150 mL) was added n-BuLi 2.5 M hexane solution (46.0 mL, 83.0 mmol). After 30 min, epoxide (10) (5.0 g, 16.6 mmol) in THF (20 mL) was introduced and the reaction slowly allowed to warm to 0° C. over 1 h; the mixture was then stirred at ambient temperature for 2 hr. The reaction was quenched with water and extracted with ethyl acetate (50 mL×2). The combined organic layers were washed with brine, dried over $Na_2SO_4$, filtered, and concentrated under vacuum. The residues were purified on silica gel column chromatography (10% EtOAc/Hexane) to give allylic alcohol 11 (4 g, 80%) as an oil. $[\alpha]^{22}_D$ − 20.35° (c 2.0, $CHCl_3$); $^1$H NMR (500 MHz, $CDCl_3$) δ 5.31 (s, 1H), 5.11 (s, 1H), 4.52 (d, J=6 Hz, 1H), 4.32-4.31 (m, 1H), 4.13-4.11 (m, 1H), 3.81-3.79 (m, 2H), 3.62-3.60 (m, 1H), 3.91-3.90 (m, 1H,), 2.62 (br, 1H), 1.30 (s, 3H), 1.20 (s, 3H), 0.80 (m, 9H), 0.013-0.006 (m, 6H); $^{13}$C NMR (125 MHz, $CDCl_3$) δ 157.9, 115.9, 92.6, 88.8, 84.1, 72.4, 59.0, 32.6, 31.5, 30.4, 24.0, 0.05; HR-MS Calcd. For $(C_{16}H_{30}O_4Si+H)^+$ 315.1913, found 315.1892.

(−)-(3aS,4S,6R,6aR)-6-(((tert-butyldimethylsilyl)oxy)methyl)-2,2-dimethyl-5-methylene-tetrahydro-3aH-cyclopenta[d][1,3]dioxol-4-ol (12). To a stirred solution of allylic alcohol 11 (4 g, 12.7 mmol) was added dess marline (8.1 g, 19.7 mmol) at 0° C. The mixture was warm to ambient temperature and stirred for 1 hr. The mixture was passed through celite bed and obtained filtrate was concentrated under reduced pressure to give crude allylic ketone, which was proceeded as such in next step without further purification.

The crude allylic ketone (3.5 g, 11.1 mmol) was dissolved in anhydrous methanol, cooled the solution at −78° C. Added $CeCl_3.7H_2O$ (5.8 g, 15.6 mmol) at −78° C. and after 10 minutes stirring $NaBH_4$ (0.54 g, 14.5 mmol) was added at one portion. After 15 min stirring at −78° C., the reaction mixture was allowed to 0° C. then saturated $NH_4Cl$ (30 mL) was added and the mixture was allowed to stir for 1 hr. Solvent was removed under reduced temperature and pressure and the residue was extracted with DCM (200 mL×2). The combined DCM extracts were washed with brine (40 mL×2), dried over anhydrous $Na_2SO_4$, filtered and concentrated under vacuum. The residue was purified by flash silica gel column chromatography (5% EtOAc/hexane) to give compound 12 (3.2 g, 80%) as oil. $[\alpha]^{22}_D$ −96.878° (c 2.01, $CHCl_3$); $^1$H NMR (500 MHz, $CDCl_3$) δ 5.26(s, 1H), 5.10 (s, 1H), 4.52 (m, 2, 3- H's, 2H), 4.4 (m, 1H, 1-H'), 3.71 (dd, J=4 & 10 Hz, 1H, 5- Ha), 3.53 (dd, J=4 & 10 Hz, 5- Hb, 1H), 2.57 (br, 1H), 2.29 (d, J=10.5 Hz, $D_2O$ exchange, OH), 1.38 (s, 3H), 1.30 (s, 3H), 0.85 (m, 9H), 0.013-0.006 (m, 6H). $^{13}$C NMR(125 MHz, $CDCl_3$) 159.01, 115.9, 115.4, 86.85, 84.85, 79.48, 71.63, 57.21, 32.13, 31.54, 30.33, 23.83, 0.015; HR-MS Calcd. For $(C_{16}H_{30}O_4Si+H)^+$ 315.1913, found 315.1987.

(−)-(3aR,4R,6S,6aS)-4-4(tert-butyldimethylsilyl)oxy)methyl)-2,2-dimethyltetrahydrospiro[cyclopenta[d][1,3]dioxole-5,1'-cyclopropan]-6-ol (13). To a solution of 12 (3 g, 9.5 mmol) in anhydrous ether (50 mL) was added diethyl zinc (1.0 M solution in hexane, 24.2 mL, 28.6 mmol) followed by diiodomethane (4.6 mL, 57.3 mmol) at 0° C. The reaction mixture was allowed to room temperature and was refluxed for 8 hr. The reaction mixture was cooled to 0° C. and quenched with saturated $NH_4Cl$ solution (20 mL) and extracted with ether (2×60 mL). The combined organic layers were washed with water (30 mL), brine (30 mL), dried over $Na_2SO_4$ and concentrated under reduced pressure. The residue was purified by column chromatography (5% EtOAc/hexane) to afford 13 (3.0 g, 93%) as an oil. $[\alpha]^{24}_D$ − 86.03° (c 2.01, $CHCl_3$); $^1$H NMR (500 MHz, $CDCl_3$) δ 4.55 (m, 1H), 4.49 (m, 1H), 4.08 (m, 1H), 3.59 (dd, J=3.0 & 9.5 Hz), 3.50 (dd, J=4.5 & 10.5 Hz, 1H), 2.22 (d, J=10.5 Hz, $D_2O$ exchange OH, 1H), 1.57 (m, 1H), 1.44 (s, 3H), 1.31 (s, 3H), 0.84 (m, 10H), 0.43 (m, 1H), 0.32 (m, 1H), 0.24 (1H), −0.06 (s, 6H). $^{13}$C NMR(125 MHz, $CDCl_3$) 159.01, 115.9, 115.4, 86.85, 84.85, 79.48, 71.63, 57.21, 32.13, 31.54, 30.33, 29.24 23.83, 7.14, 0.015; HR-MS Calcd. For $(C_{17}H_{32}O_4Si)^+$ 328.2070, found 328.2195.

(−)-(3aS,4R,6R,6aR)-6-(((tert-butyldimethylsilyl)oxy)methyl)-2,2-dimethyltetrahydrospiro[cyclopenta[d][1,3]dioxole-5,1'-cyclopropan]-4-amine (14). Compound 13 (0.5 g, 1.52 mmol) and $PPh_3$ (0.8 g, 3.04 mmol) were dissolved in anhydrous THF (20 mL), diisopropylethylamine (0.5 mL, 3.04 mmol) was added and the mixture cooled to 10° C. DIAD (0.62 mL, 3.04 mmol) was then added slowly over 15 min at temperature 10° C. and the reaction mixture stirred for 10 min. DPPA (0.66 mL, 3.08 mmol) was then added drop wise over 10 min at 15° C., and the reaction mixture was warmed to 25° C. over a period of 30 minute, stirred for addition 2 hr. Mixture was quenched with methanol concentrated on reduced pressure, residue was purified by the column chromatography (3% EtOAc/hexane) to give the azide intermediate as an oil. IR 2097 cm$^{-1}$; $^1$H NMR (500 MHz, $CDCl_3$) δ 4.65(d, J=8 Hz, 1H), 4.47 (d, J=7.5 Hz, 1H), 3.67-4.58 (m, 1H), 1.80-1.77 (m, 1H), 1.48 (s, 3H), 1.31 (s, 3H), 1.20 (s, 3H), 0.91-0.86 (m, 9H), 0.79-0.77 (m, 1H, cp), 0.72-0.0.69 (m, 2H, cp), 0.68-0.65(m, 1H, cp), 0.06-0.05(m, 6H). A suspension of azido intermediate (0.4 g, 2.33 mmol) and 10% Pd/C (330 mg) in absolute EtOH was shaken under 30 psi of $H_2$ at room temperature for 2 hr. Celite was added into the solution and the slurry was filtered through a celite pad. The volatile was removed in vacuo and the residue was purified by column chromatography on silica gel (2% MeOH/DCM) to give 14 (0.86 g, 95%) as an oil. $^1$H NMR (500 MHz, $CDCl_3$): δ 4.58 (dd, J=1.5 & 6.0 Hz, 1H), 4.29(dd, J=1.0 & 6.0 Hz), 3.67(m, 2H), 2.76(m, 1H), 1.78(m, 1H), 1.49(s, 3H), 1.31(s, 3H), 0.90(s, 9H), 0.68(m, 1H), 0.60(m, 1H), 0.48(m, 2H), 0.003(s, 6H); $^{13}$C (125 MHz, $CDCl_3$): δ 0.000, 7.31, 21.022, 23.82, 30.22, 31.44, 32.33, 34.06, 60.07, 69.41, 70.23, 89.09, 93.94, 115.65. HR-MS Calcd. For $(C_{17}H_{33}NO_3Si)^+$ 328.2230, found 328.2568.

(−)-1-((3aR,4R,6R,6aS)-4-(((tert-butyldimethylsilyl)oxy)methyl)-2,2-dimethyltetrahydrospiro[cyclopenta[d][1,3]dioxole-5,1'-cyclopropan]-6-yl)pyrimidine-2,4(1H,3H)-dione (16). To a suspension of silver cynate (0.81 g, 5.5 mmol) in anhydrous benzene (20 mL), β-methoxyacryloyl chloride (0.6 g, 5.4 mmol) was added. The mixture was heated under reflux for 30 minutes and cooled to room temperature. The supernatant solution was added into the solution of amine 14 (0.7 g, 2.1 mmol) in anhydrous THF (30 mL) at −30° C. during 15 minutes. The mixture was allowed to gradually warm up to room temperature and kept overnight. After removing the solvent in vacuo, the residue was purified by column chromatography on silica gel (30% EtOAc/Hexane) to give crude 15 (0.6 g) as a yellow syrup which was directly used for next step. Crude compound 15 (0.6 g) was dissolved in 1,4-dioxane/ethanol (20 mL/20 mL) and treated with 28% solution of ammonium hydroxide (20 mL) in a steel bomb at 90-100° C. for 17 hr. After removing the solvent in vacuo, the residue was purified by column chromatography on a silica gel (2% MeOH/DCM) to give 16 (0.36 g, 41%) as a pale yellow syrup. $[\alpha]^{22}_D$ − 86.03 (c 2.01, CHCl$_3$); $^1$H NMR (500 MHz, CDCl$_3$) δ 8.81(brs, 1H, NH), 7.64 (d, J=8.0 Hz, 1H), 5.56 (d, J=8.0 Hz, 1H), 4.68 (m, 1H), 4.47 (m, 2H), 3.54 (m, 2H), 2.08 (m, 1H), 1.50 (s, 3H), 1.25 (s, 3H), 0.80 (m, 11H), 0.72 (m, 1H), 0.26 (m, 1H), 0.003 (s, 6H); $^{13}$C (125 MHz, CDCl$_3$): δ −5.43, 7.82, 16.47, 18.39, 24.48, 25.94, 27.58, 52.13, 62.68, 82.28, 85.92, 101.74, 111.72, 143.46, 150.96, 163.02; HR-MS Calcd. For $(C_{17}H_{32}O_4Si)^+$ 328.2070, found 328.2295.

(−)-1-((4R,5S,6R,7R)-5,6-dihydroxy-7-(hydroxymethyl) spiro[2.4]heptan-4-yl)pyrimidine-2,4(1H,3H)-dione (17). Compound 16 (0.2 g, 0.47 mmol) was dissolved in 20 mL of CF$_3$COOH/H$_2$O (2:1, v/v) and heated to 50° C. for 3 hr. The solvent was removed under vacuum and the residue was co-evaporated with ethanol (10 mL×3) under vacuum. The residue was purified by column chromatography on a silica gel (7% MeOH/CH$_2$Cl$_2$) to give 17 (100 mg, 79%) as white foam. mp 114-116° C.; $[\alpha]^{24}_D$ 9.84° (c 0.26, MeOH); UV(MeOH) λ$_{max}$ 265 nm (ε 11713, pH 2), 265 nm (ε 11887, pH 7), 264 nm (ε 9153, pH 11); $^1$H NMR (500 MHz, CD$_3$OD-d$_6$) δ 7.50 (d, J=8.5 Hz, 1H), 5.68 (d, J=8.5 Hz, 1 H), 4.77-4.73 (m, 2 H), 4.62 (d, J=3 Hz, 1 H), 3.71 (dd, J=4.5 & 11.0 Hz, 1 H), 3.62 (dd, J=5 & 11.0 Hz, 1 H), 2.26 (m, 1 H), 0.87 (m, 2H), 0.81 (m, 1H), 0.33 (m, 1H); $^{13}$C NMR (125 MHz, CD$_3$OD) δ 165.1, 152.2, 146.3, 109.9, 74.3, 72.4, 63.4, 51.1, 29.8, 28.7, 10.9; HR-MS Calcd. For $(C_{12}H_{16}N_2O_5+H)^+$ 269.1059, found 269.1261.

General Procedure for Synthesis of Prodrug 18, 19, and 20

N-Methylimidazole (NMI, 5.0 mmol) was added to a stirring suspension compound 17 (1 mmol) in dry THF under argon atmosphere at −78° C. The appropriate substituted chlorophenylphosphoryl-L-alaninate (3.0 mmol) dissolve in THF was added drop wise, slowly heated up to room temperature and continue stirred over night at room temperature. Volatiles were evaporated, and the residue was dissolved in dichloromethane (DCM) and washed with 0.5 N HCl. The organic layer dried over Na$_2$SO$_4$ filtered, concentrated to dryness under reduced pressure, and the residue was purified by flash chromatography to give the prodrugs of compound 17 (18, 19 & 20).

(−)-(2R)-isopropyl 2-(((((4R,5R,6S,7R)-7-(2,4-dioxo-3,4-dihydropyrimidin-1(2H)-yl)-5,6-dihydroxyspiro[2.4]heptan-4-yl)methoxy)(phenoxy)phosphoryl)amino)propanoate (18). $^1$H NMR (500 MHz, DMSO-d$_6$) δ 11.17 (bs, 1 H, NH), 7.68 (d, J=6.8 Hz, 1 H), 7.34-7.15 (m, 5H), 5.00 (d, J=6 Hz, 1 H), 4.74-4.78 (bs, 2 H, —OH), 4.70 (d, J=4 Hz, 1 H), 4.68 (d, J=7.6 Hz, 1H), 4.21 (m, 1H); 4.11 (m, 2H), 3.93-3.90 (m, 1 H), 3.32-3.43 (m, 2 H), 1.78-1.81 (m, 1 H), 1.40 (d, J=6.5 Hz, 3 H); 1.28 (d, J=14.0 Hz, 6H); 0.69-0.74 (m, 1 H, -cp), 0.49-0.56 (m, 2 H, -cp), 0.00-0.04 (m, 1 H, -cp); $^{13}$C NMR (500 MHz, DMSO-d$_6$) δ 171.6, 164.9, 161.4, 154.3 153.6, 152.3, 140.2, 109.6, 76.0, 74.0, 60.2, 51.4, 29.4, 28.6, 21.1, 14.7, 11.0, 7.3; $^{31}$P NMR (CDCl$_3$, 202 MHz): δ 2.67, 2.99. HR-MS Calcd. For $(C_{24}H_{32}N_3O_9P+H)^+$ 537.1876, found 537.1942.

Figure 3:
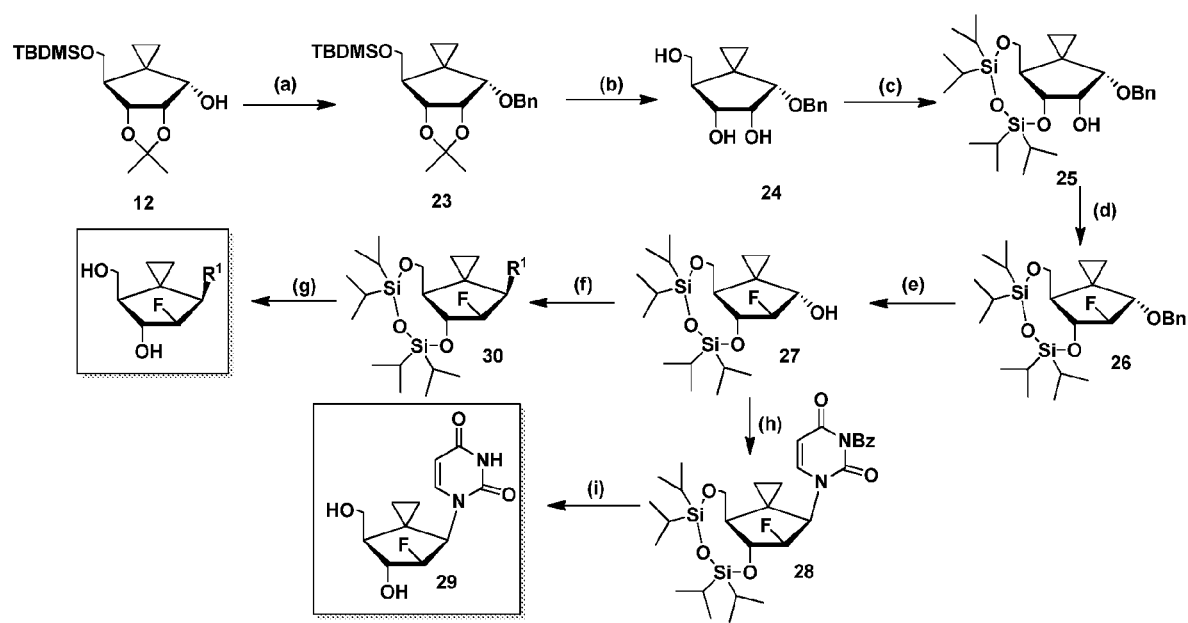

Detailed Synthetic Protocols for FIG. 3

(−)-(((3aR,4S,6R,6aR)-4-(benzyloxy)-2,2-dimethyltetrahydrospiro[cyclopenta[d][1,3]dioxole-5,1'-cyclopropan]-6-yl)methoxy)(tert-butyl)dimethylsilane (23). To a stirred solution of 12 (5.5 g, 16.7 mmol) in anhydrous DMF (50 mL) was added NaH in 60% mineral oil (0.8 g, 20.1 mmol), at 0° C. under argon. After 30 minutes benzyl bromide (2.36 mL, 20.1 mmol) was added drop wise at same temperature. The mixture was stirred for 3 hr at room temperature. It was quenched with ice-cold water (50 mL) and extracted with diethyl ether (2×300 mL). The combined extracts were washed with water (200 mL), brine (100 mL) and dried over Na$_2$SO$_4$. The solvent was removed under reduced pressure and the residue was purified by flash silica gel column chromatography (EtOAc:Hexane 1:10 to 3:10) to give fully protected carbocyclic intermediate 24 (5.6 g 80%) as oil. $[\alpha]^{24}_D$ −121.09° (c 0.83, CHCl$_3$); $^1$H NMR (500 MHz, CDCl$_3$) δ 7.43 (m, 5H), 4.83 (d, J=12.5 Hz, 1H), 4.68 (d, J=12.5 Hz, 1H), 4.56 (t, J=5.5 Hz, 1H), 4.44 (d, J=6.0 Hz, 1H), 4.30 (m, 1H), 3.42 (dd, J=4.0, 8.5 Hz, 1H), 3.21 (dd, J=5.0, 8.5 Hz, 1H), 2.59-2.57 (m, 1H), 1.46 (s, 3H), 1.34 (s, 3H), 0.84 (m, 10H), 0.43 (m, 1H), 0.32 (m, 1H), 0.24 (m, 1H), −0.06 (s, 6H); $^{13}$C NMR (125 MHz, CDCl$_3$) δ 150.6, 138.6, 127.8, 110.8, 108.9, 81.3, 79.7, 78.5, 72.6, 71.8, 64.5, 49.9, 32.13, 31.54, 30.33, 29.24 23.83, 7.14, 0.015; HR-MS Calcd. For $(C_{21}H_{30}O_4+H)^+$ 419.2539, found 419.2831.

(−)-(4S,5R,6R,7R)-4-(benzyloxy)-7-(hydroxymethyl) spiro[2.4]heptane-5,6-diol (24) The fully protected resultant carbocyclic intermediate 23 (5.6 g, 13.3 mmol) was dissolved in 100 mL of CF$_3$CO$_2$H/H$_2$O (2:1, v/v) and heated to 50° C. for 3 h. The solvent was removed under vacuum and the residue was co-evaporated with ethanol (3×50 mL). The residue dissolved in methanol (100 mL) and passed ammonia gas at 0° C. for 5 minutes for neutralization. After removal of the solvent the residue was purified by silica gel column chromatography (3% MeOH/DCM) to give 5 (2.9 g, 82%) as a white solid. mp 122-124° C.; $[\alpha]^{24}_D$ −123.05° (c 0.37, MeOH); $^1$H NMR (500 MHz, CD$_3$OD) δ 7.46-7.30 (m, 5 H,), 4.77 (d, J=12 Hz, 1 H), 4.62 (d, 12.5 Hz, 1H), 4.17-4.14 (m, 2 H), 3.95-3.93 (m, 1 H), 3.82-3.73 (m, 2H), 2.69-2.66 (m, 1 H), 0.61 (m, 1H), 0.43 (m, 1H), 0.32 (m, 1H), 0.24 (m, 1H); $^{13}$C NMR (125 MHz, CDCl$_3$) δ 148.9, 138.3, 128.0, 109.1, 80.8, 71.7, 71.0, 70.8, 61.8, 49.6, 29.24 23.83, 7.14; HR-MS Calcd. For $(C_{15}H_{20}O_4+H)^+$ 265.1362, found 265.1410.

(−)-(6aR,8S,9S,9aR)-8-(benzyloxy)-2,2,4,4-tetraisopropyltetrahydro-6H-Spiro[cyclo-penta[f][3,5,2,4]trioxadisilocine-7,1'-cyclopropan]-9-ol (25). To a stirred mixture of triol 24 (2.9 g, 10.9 mmol) and imidazole (5.2 g, 76.8 mmol) in DMF (80 mL) at 0° C. under argon was added dropwise 1,3-dichloro-1,1,3,3-tetraisopropyldisiloxane (3.5 mL, 11.0 mmol). After the mixture was stirred at room temperature for 1 h, quenched with MeOH (15 mL) and water (100 mL) was added and the mixture was extracted with EtOAc (2×200 mL). The combined organic layers were washed with brine (40 mL) dried over Na$_2$SO$_4$. The solvent was removed and the residue was purified by silica gel column chromatography (EtOAc:Hexane 1:30 to 1:5) to give 25 (5.1 g, 92%) as an oil. $[\alpha]^{24}_D$ −105.94° (c 0.58, CHCl$_3$); $^1$H NMR (500 MHz, CDCl$_3$) δ 7.41-7.26 (m, 5H), 4.77 (d, J=12 Hz, 1H), 4.62 (d, J=12 Hz, 1H), 4.18-4.14 (m, 3H), 4.05 (dd, J=4.5, 12.0 Hz, 1H), 3.78 (dd, J=8, 12 Hz, 1H), 2.89 (m, 1 H), 2.78 (d, J=2.0 Hz, 1H, OH) 1.08-0.97 (m, 28H), 0.61 (m, 1H), 0.43 (m, 1H), 0.32 (m, 1H), 0.24 (m, 1H); $^{13}$C NMR (125 MHz, CDCl$_3$) δ 154.0, 147.3, 138.1, 128.4, 80.2, 74.2, 71.2, 71.1, 64.9, 50.1, 29.24 23.83, 17.6, 17.5, 17.4, 17.3, 17.2, 17.1, 17.0, 16.9, 16.8, 13.4, 12.9, 12.7, 12.5, 7.20; HR-MS Calcd. For $(C_{27}H_{46}O_5Si_2+H)^+$ 507.2884, found 507.2798.

(−)-(6aR,8S,9R,9aR)-8-(benzyloxy)-9-fluoro-2,2,4,4-tetraisopropyltetrahydro-6H-Spiro[cyclopenta[f][1,3,5,2,4]trioxadisilocine-7,1'-cyclopropane] (26)

To a solution of alcohol 25 (5.1 g, 10.7 mmol) in anhydrous $CH_2Cl_2$, (diethylamino) sulfur trifluoride (DAST) (9.3 ml, 70.5 mmol) was added slowly at room temperature. The reaction mixture was quenched with iced $H_2O$ after 20 min. The organic layer was collected and the aqueous phase was extracted with dichloromethane. The organic layer was then combined, dried over $Na_2SO_4$ and the volatiles removed under reduced pressure. The crude residue was purified by flash silica gel column chromatography (1% EtOAc/Hexane) to give 26 (2.5 g, 49%). $[\alpha]24_D$ −98.08° (c 0.51, $CHCl_3$); $^1H$ NMR (500 MHz, $CDCl_3$) δ 7.39-7.26 (m, 5H), 4.92 (ddd, J=6.0, 7.5 & 5.5 Hz, 1H), 4.78 (d, J=11.5 Hz, 1H), 4.65 (d, J=11.5 Hz, 1H), 4.31-4.26 (m, 1H), 4.23-4.16 (m, 1H), 4.01-3.92 (m, 2H), 2.70 (m, 1H) 1.08-0.94 (m, 28H), 0.72 (m, 1H), 0.68-0.43 (m, 2H), 0.28 (m, 1H); $^{13}C$ NMR (125 MHz, $CDCl_3$) δ 142.6 (d, J=9.2 Hz), 141.8, 137.9, 128.4, 112.7, 103.4 (d, J=189.0 Hz), 80.4 (d, J=21.3 Hz), 73.8 (d, J=19.8 Hz), 71.3, 61.6, 48.8 (d, J=5.3 Hz), 29.4, 24.5, 17.5, 17.4, 17.3, _17.2, 17.1, 17.0, 16.9, 16.8, 13.4, 13.3, 12.7, 12.5, 7.9; HR-MS Calcd. For $(C_{27}H_{45}FO_4Si_2+H)^+$ 509.2840, found 509.2923.

(−)-(6aR,8S,9R,9aR)-9-fluoro-2,2,4,4-tetraisopropyltetrahydro-6H-spiro[cyclopenta[f][1,3,5,2,4]trioxadisilocine-7,1'-cyclopropan]-8-ol. (27). A solution of compound 26 (1.38 g, 2.6 mmol) in anhydrous $CH_2Cl_2$ was treated with boron trichloride (7.1 ml, 1M solution in $CH_2Cl_2$, 8.1 mmol) at −78° C. during 15 minute. After stirred at the same temperature for another 15 min, additional portion of boron trichloride (5.1 mL of 1M solution in $CH_2Cl_2$) was added. The reaction was quenched with MeOH at −78° C. after 15 min and concentrated under reduced pressure. The residue was purified by column chromatography on the silica gel (EtOAc:Hexane=1:10 to 1:3) to give 27 (0.84 g, 78%). $[\alpha]^{24}_D$ −53.55° (c 0.5, MeOH); $^1H$ NMR (500 MHz, $CDCl_3$) δ 4.65 (dt, J=8.0 & 15.0 Hz, 1H), 4.49-4.45 (m, 1H), 4.26-4.21 (m, 1H), 3.99 (dd, J=4.5 & 12.0 Hz, 1H), 3.89 (dd, J=6.0 & 11.5 Hz, 1H), 2.66 (s, 1H), 0.93-1.08 (m, 28H), 0.72 (m, 1H), 0.68-0.43 (m, 2H), 0.28 (m, 1H); $^{19}F$ NMR (500 MHz, $CDCl_3$) δ −195.8 (m); $^{13}C$ NMR (125 MHz, $CDCl_3$) δ 7.8, 12.5, 12.7, 13.3, 13.4, 16.9, 16.98, 17.07, 17.08, 17.4, 17.5, 27.5 29.8, 49.1, 63.7, 73.7, 74.7, 102.3 (d, J=192.7 Hz); HR-MS Calcd. For $(C_{20}H_{39}FO_4Si_2+H)^+$ 418.2592, found 418.2592.

(−)-3-benzoyl-1-((6aR,8R,9R,9aR)-9-fluoro-2,2,4,4-tetraisopropyltetrahydro-6H-spiro[cyclopenta[f][1,3,5,2,4]trioxadisilocine-7,1'-cyclopropan]-8-yl)pyrimidine-2,4(1H,3H)-dione (28). To a stirred solution of triphenylphosphine (0.37 g, 1.43 mmol), in THF (5 mL) at −10° C. was added dropwise the DIAD (0.26 mL, 1.43 mmol) and the reaction mixture was stirred at this temperature for 30 min. After that a solution of benzoyl protected uracil base (0.15 g, 0.7 mmol) in THF (5 mL) was added and stirred for 30 minute at 0° C. Compound 27 (0.2 g, 0.47 mmol) in THF (5 mL) was added and the reaction was stirred for 3 hours at room temperature. The volatiles were removed under reduced pressure and the residue was purified by the silica gel column chromatography (EtOAc:hexane=1:20 to 1:10) to give 28 (200 mg, 51%) as colorless oil. UV (MeOH) $\lambda_{max}$ 264 nm, (pH 7); 266.0 nm (pH 12); $^1H$ NMR (500 MHz, $CDCl_3$) δ 7.86 (d, J=12.5 Hz, 1H) 7.65-7.44 (m, 5H), 5.89 (d, J=30.5 Hz, 1H), 5.76 (d, J=14.5 Hz, 1H), 4.80 (m, 1H), 4.65 (m, 1H), 3.44-3.22 (m, 2H), 2.39 (m, 1H), 1.11-1.09 (m, 28H), 0.72 (m, 1H), 0.68-0.43 (m, 2H), 0.28 (m, 1H); $^{19}F$ NMR (500 MHz, $CDCl_3$) δ −192.87 (m); $^{13}C$ NMR (125 MHz, $CDCl_3$) δ 162.2, 153.6, 152.2, 144.1, 133.9, 128.6, 113.4, 93.4, (d, J=187.5 Hz), 83.9, 76.0 (d, J=50.0 Hz), 64.3, 58.5, 29.8, 27.8, 17.08, 17.07, 17.05, 16.09, 16.06, 13.05, 13.03, 8.1; HR-MS Cald. For $(C_{31}H_{45}FN_2O_6Si_2+H)^+$ 617.2800, found 617.2917.

1-((4R,5R,6R,7R)-5-fluoro-6-hydroxy-7-(hydroxymethyl)spiro[2.4]heptan-4-yl)pyrimidine-2,4(1H,3H)-dione (29). Compound 28 (0.2 g, 0.32 mmol) was dissolved in saturated MeOH with $NH_3$ (20 mL) and stirred for 8 h at room temperature. The solvent was evaporated under vacuum and the residue was purified by silica gel vacuum column (35% EtOAc/hexane) to give the debenzolated compound. Debenzoylated compound was dissolved in 10 mL of $CF_3COOH$/$H_2O$ (2:1, v/v) and heated to 50° C. for 3 h. The solvent was removed under vacuum and the residue was co-evaporated with ethanol (3×10 mL) under vacuum. The residue was purified by combiflash chromatography (7% $MeOH/CH_2Cl_2$) to give 29 in 60 mg (68%) as white foam. $[\alpha]^{24}_D$ 5.4° (c 0.67, MeOH); $^1H$ NMR (500 MHz, DMSO-$d_6$) δ 11.17 (bs, 1 H), 7.68 (d, J=15.6, 1 H), 5.80 (d, J=19.7, 1H), 5.67 (d, J=14.5 Hz, 1 H), 4.74-4.78 (bs, 2 H, —OH), 4.70 (m, 1H), 4.10-4.13 (bm, 1 H, —OH), 3.32-3.43 (m, 2 H), 2.1-2.08 (m, 1 H), 0.69-0.74 (m, 1 H), 0.49-0.56 (m, 2 H), 0.43 (m, 1 H); $^{13}C$ NMR (500 MHz, MeOH-d4) δ 164.9, 161.4, 152.3, 140.2, 109.6, 76.0, 74.0, 60.2, 51.4, 21.1, 14.7, 11.0, 7.3; HR-MS Cald. For $(C_{12}H_{15}FN_2O_4+H)^+$ 270.16, found 270.1226.

Figure 4:
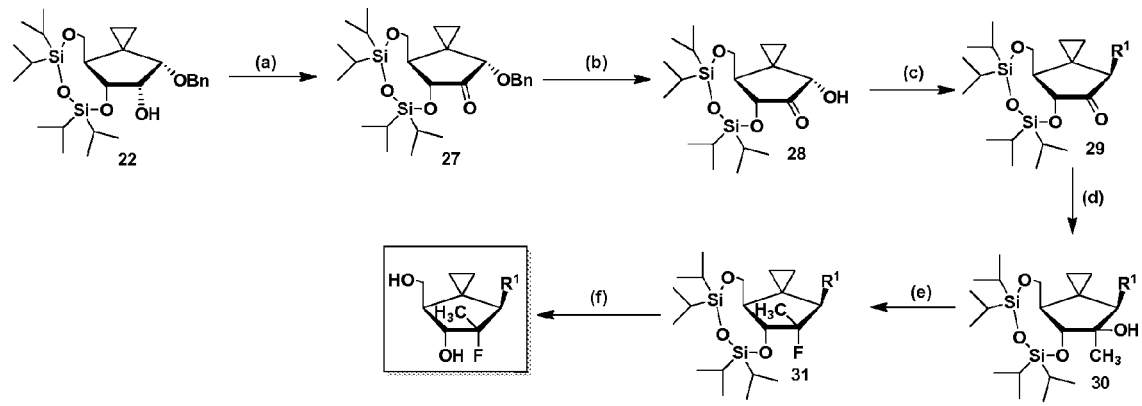
Figure 5:
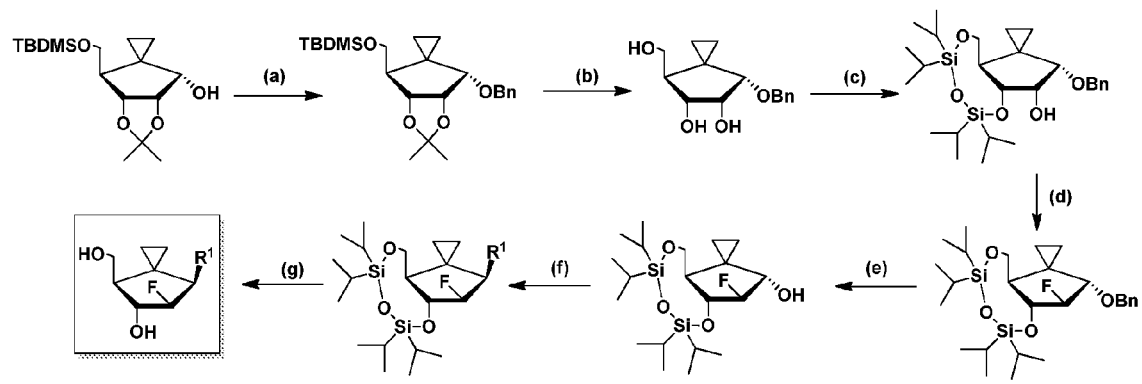
Figure 6:
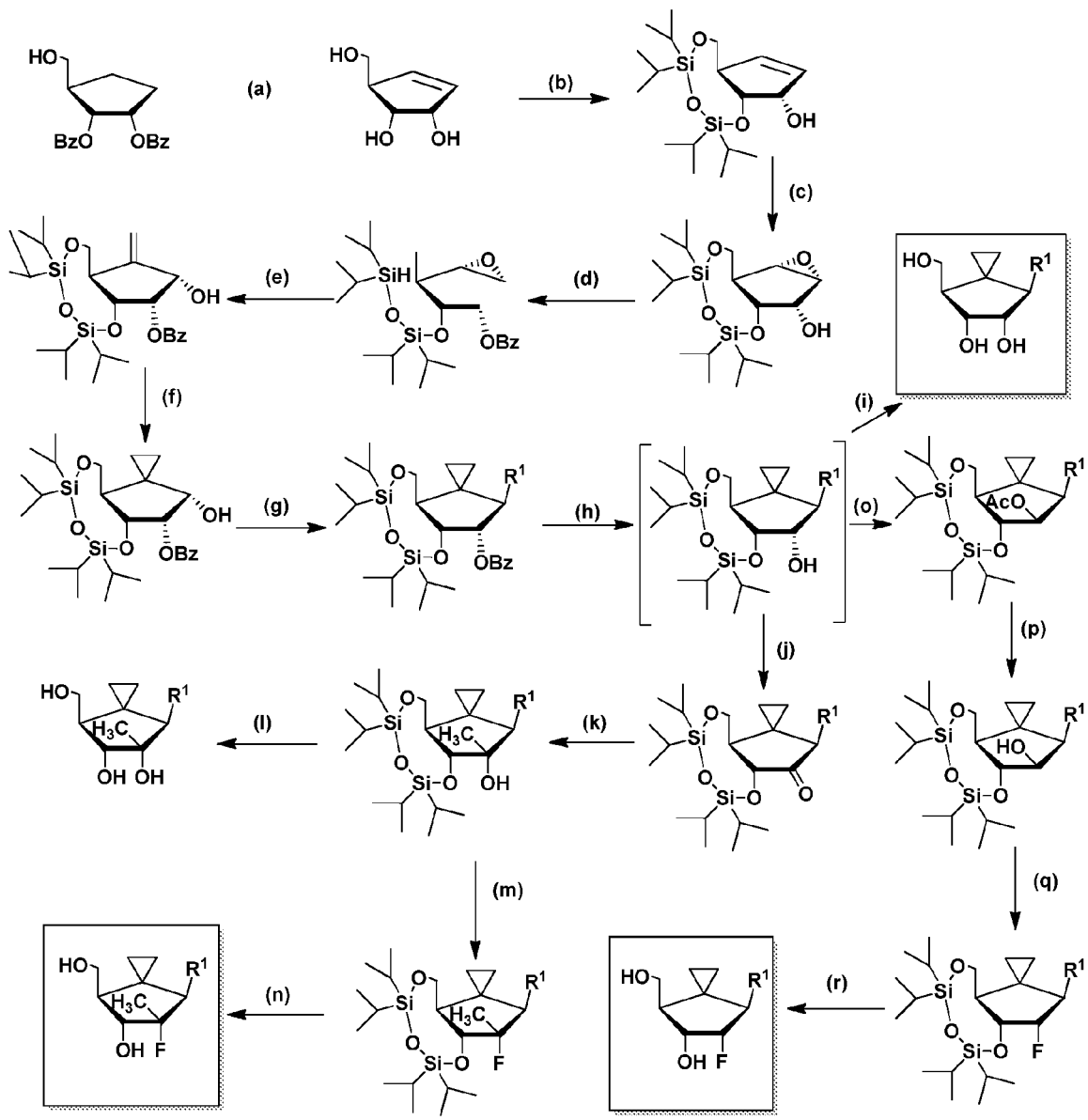
Figure 7:
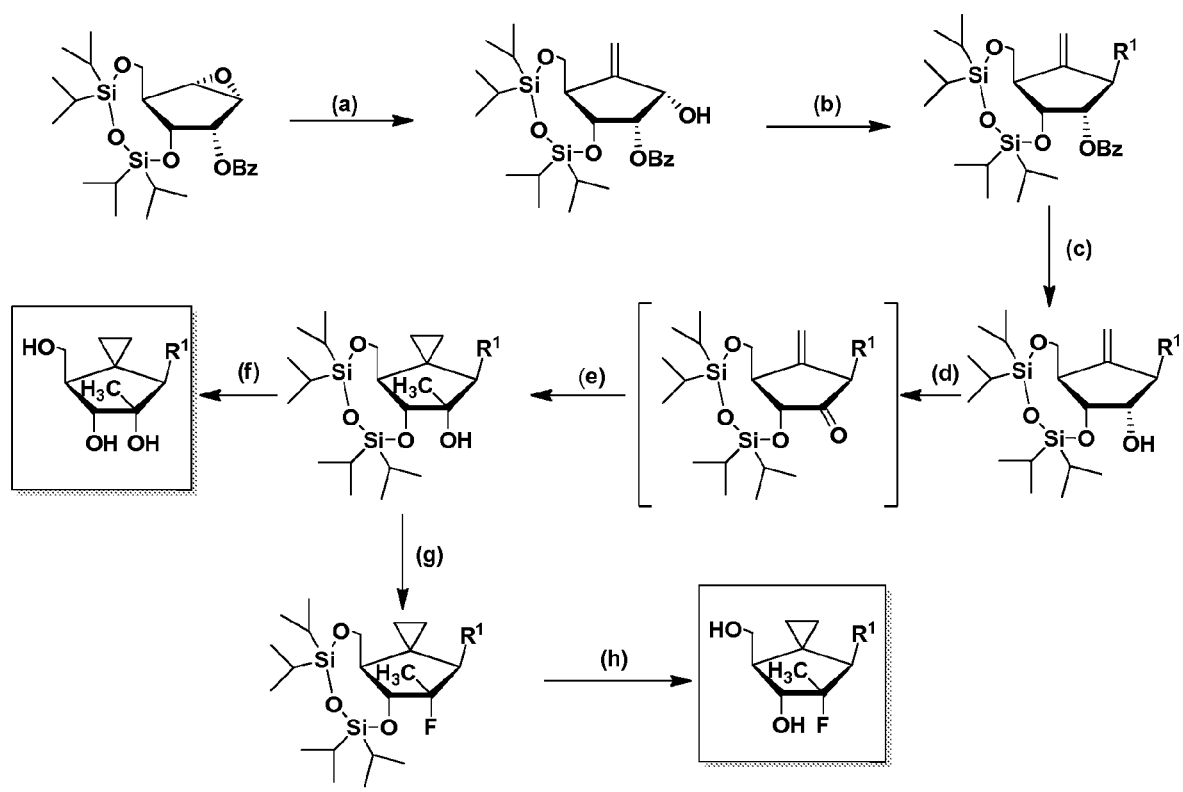
Figure 8:
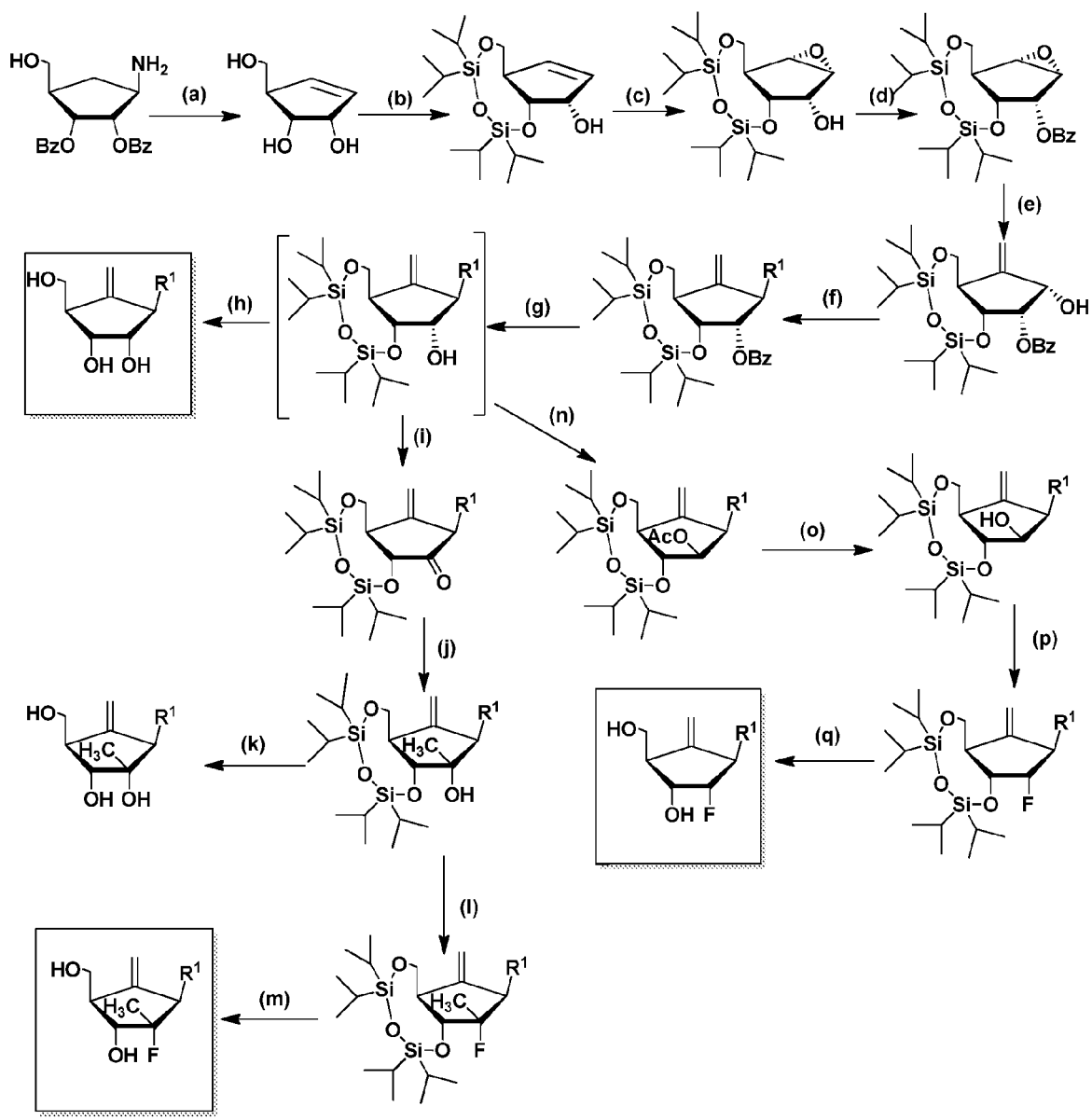
Figure 9:
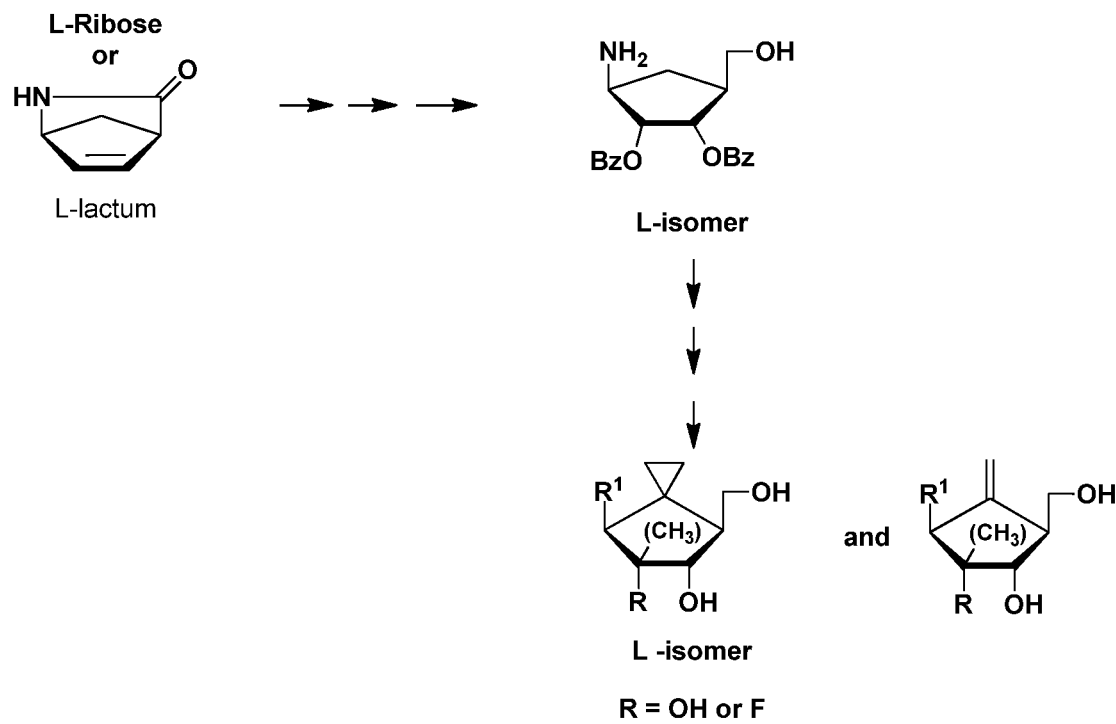
Figure 10:
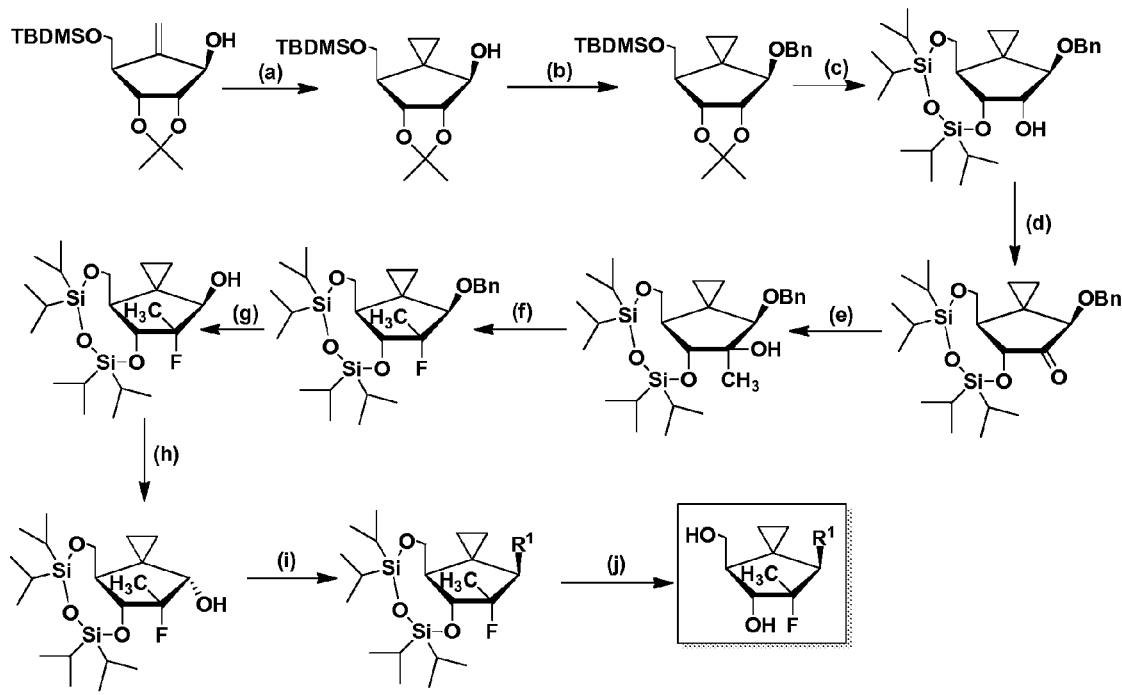
Figure 11:
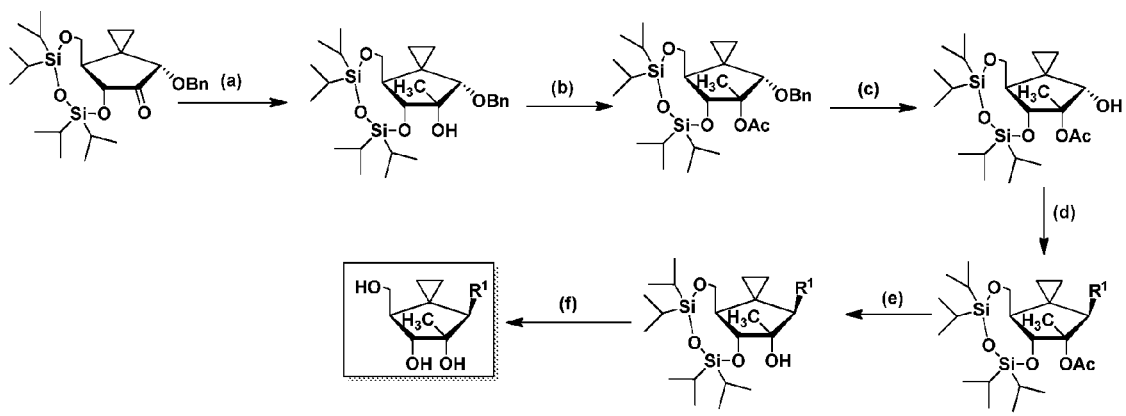

Detailed Synthetic Protocols for FIG. 4

(−)-(6aR,8S,9aR)-8-(benzyloxy)-2,2,4,4-tetraisopropyldihydro-6H-spiro[cyclo penta[f][1,3,5,2,4]trioxadisilocine-7,1'-cyclopropan]-9(6aH)-one (31). To a stirred solution of alcohol 11 (4 g, 7.9 mmol) was added dess marline (4.0 g, 9.4 mmol) at 0° C. The mixture was warm to ambient temperature and stirred for 1 hr. The mixture was passed through celite bed and obtained filtrate was concentrated under reduced pressure. The residue was purified by column chromatography on a silica gel (2% EtOAc/hexane) to give ketone 31 (3.5 g, 89%) as an oil. $[\alpha]^{24}_D$ −98.94° (c 0.58, $CHCl_3$); $^1H$ NMR (500 MHz, $CDCl_3$) δ 7.41-7.26 (m, 5H), 4.62 (d, J=12 Hz, 1H), 4.42 (d, J=12 Hz, 1H), 4.18-4.14 (m, 2H), 4.05 (dd, J=4.5, 12.0 Hz, 1H), 3.78 (dd, J=8, 12 Hz, 1 H), 1.98 (m, 1 H), 1.08-0.97 (m, 28H), 0.61 (m, 1H), 0.43 (m, 1H), 0.32 (m, 1H), 0.24 (m, 1H); $^{13}C$ NMR (125 MHz, $CDCl_3$) δ 162.4, 154.0, 147.3, 138.1, 128.4, 80.2, 74.2, 71.2, 64.9, 50.1, 29.24 23.83, 17.6, 17.5, 17.4, 17.3, 17.2, 17.1, 17.0, 16.9, 16.8, 13.4, 12.9, 12.7, 12.5, 7.20; HR-MS Calcd. For $(C_{27}H_{44}O_5Si_2+H)^+$ 505.2727, found 505.2798.

(−)-(6aR,8S,9aR)-8-hydroxy-2,2,4,4-tetraisopropyldihydro-6H-spiro[cyclopenta[f][1,3,5,2,4]trioxadisilocine-7,1'-cyclopropan]-9(6aH)-one (32). A solution of compound 31 (3.5 g, 6.9 mmol) in anhydrous $CH_2Cl_2$ was treated with boron trichloride (20.5 ml, 1M solution in $CH_2Cl_2$, 21.5 mmol) at −78° C. during 15 minute. After stirred at the same temperature for another 15 min, additional portion of boron trichloride (6.8 mL of 1M solution in $CH_2Cl_2$, 7.1 mmol) was added. The reaction was quenched with MeOH at −78° C. after 15 min and concentrated under reduced pressure. The residue was purified by column chromatography on the silica gel (EtOAc:Hexane=1:10 to 1:3) to give 27 (0.84 g, 78%). $[\alpha]^{24}_D$ −76.54° (c 0.5, MeOH); $^1H$ NMR (500 MHz, $CDCl_3$) δ 4.49 (d, J=8.0, 1H), 4.23-4.12 (m, 1H), 3.99 (dd, J=4.5 & 12.0 Hz, 1H), 3.89 (dd, J=6.0 & 11.5 Hz, 1H), 2.39 (m, 1H), 0.93-1.08 (m, 28H), 0.72 (m, 1H), 0.68-0.43 (m, 2H), 0.28 (m, 1H); $^{19}F$ NMR (500 MHz, $CDCl_3$) δ −195.8 (m); $^{13}C$ NMR (125 MHz, $CDCl_3$) δ 7.8, 12.5, 12.7, 13.3, 13.4, 16.9, 16.98, 17.07, 17.08, 17.4, 17.5, 27.5 29.8, 49.1, 63.7, 74.7, 84.2, 164.2; HR-MS Calcd. For $(C_{20}H_{38}O_5Si_2+H)^+$ 414.2258, found 414.2362.

Biological Data

The spiro[2.4]heptanes described herein exhibit significant anti-Flaviviridae, for example, anti-HCV activity. Compounds according to the present invention can be assayed for anti-Flaviviridae activity, especially anti-HCV activity, using well-known and conventional assays found in the literature.

For example, anti-HCV activity and cytotoxicity of the compounds may be measured in the HCV subgenomic RNA replicon assay system in Huh7 ET cells. (See, Korba, et al., *Antiviral Research* 2008, 77, 56). The results may be summarized in comparison to a positive control, 2'-C-Me-cytosine {2'-C-Me-C} (Pierra, et al., *Journal of Medicinal Chemistry* 2006, 49, 6614.

Another in-vitro assay for anti-hepatitis C activity is described in U.S. Pat. No. 7,718,790 by Stuyver, et al., and assigned to Pharmasset, Inc.

There are numerous literature assays for Dengue fever, West Nile encephalitis, Tick-borne encephalitis, and Yellow fever, including Stahla, et al., "Identification of a Novel Antiviral Inhibitor of the Flavivirus Guanylyltransferase Enzyme", Journal of Virology, August 2012, Vol 86 (16), pp 8730-8379.

This specification has been described with reference to embodiments of the invention. Given the teaching herein, one of ordinary skill in the art will be able to modify the invention for a desired purpose and such variations are considered within the scope of the invention.

We claim:

1. A spiro[2.4]heptane of the structure:

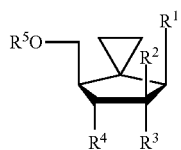

wherein:
$R^1$ is a natural or non-natural heteroaryl or heterocyclic moiety;
$R^2$ is methyl, F, Cl, $N_3$, or $OR^7$;
$R^3$ is methyl, F, Cl, or $N_3$;
$R^4$ is $OR^7$, H, methyl, F, Cl, or $N_3$;
$R^5$ is H, phosphate, a stabilized phosphate prodrug, phosphoramidate, acyl, alkyl, sulfonate ester, a lipid, a phospholipid, an amino acid, a carbohydrate, a peptide, a cholesterol, or other pharmaceutically acceptable leaving group which when administered in vivo is capable of providing a compound wherein $R^5$ is H or mono, di, or tri-phosphate; and,
$R^7$ is H, acyl, phosphate, sulfate, amino acid, peptide, or an oxygen-protecting group;
or its pharmaceutically acceptable salt.

2. The spiro[2.4]heptane of claim 1, wherein $R^1$ is a pyrimidine or purine.

3. The spiro[2.4]heptane of claim 2, wherein the purine or pyrimidine is selected from the group consisting of cytosine, 5-halocytosine, uracil, 5-halouracil, 5-methylcytosine, thymine, adenine, thymine, guanine, xanthine, or hypoxanthine.

4. The spiro[2.4]heptane of claim 3, wherein the pyrimidine is 5-fluorocytosine or 5-fluorouracil.

5. The spiro[2.4]heptane of claim 3, wherein the pyrimidine is uracil.

6. The spiro[2.4]heptane of claim 3, wherein the pyrimidine is cytosine.

7. The spiro[2.4]heptane of claim 1, wherein $R^5$ is a phosphoramidate.

8. The spiro[2.4]heptane of claim 1, wherein $R^2$ is methyl, $R^3$ is F, and $R^4$ is $OR^7$.

9. The spiro[2.4]heptane of claim 8, wherein $R^1$ is uracil.

10. The spiro[2.4]heptane of claim 9, wherein $R^5$ is phosphoramidate.

11. The spiro[2.4]heptane of claim 1, wherein $R^3$ is F or $R^2$ is F.

12. The spiro[2.4]heptane of claim 1, wherein $R^4$ and $R^5$ together form a bridge.

13. The spiro[2.4]heptane of claim 12, wherein the bridge is selected from a phosphoester, carbodiester, or a phosphoramidate.

14. Spiro[2.4]heptanes of the formula:

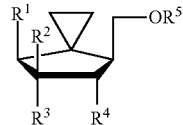

wherein $R^1$, $R^2$, $R^3$, $R^4$, $R^5$, and $R^7$ are as defined in claim 1, or a pharmaceutically acceptable salt thereof.

15. The spiro[2.4]heptane of claim 14, wherein $R^1$ is a pyrimidine or purine.

16. The spiro[2.4]heptane of claim 15, wherein the purine or pyrimidine is selected from the group consisting of cytosine, 5-halocytosine, uracil, 5-halouracil, 5-methylcytosine, thymine, adenine, thymine, guanine, xanthine, or hypoxanthine.

17. The spiro[2.4]heptane of claim 16, wherein the pyrimidine is 5-fluorocytosine or 5-fluorouracil.

18. The spiro[2.4]heptane of claim 16, wherein the pyrimidine is uracil.

19. The spiro[2.4]heptane of claim 16, wherein the pyrimidine is cytosine.

20. The spiro[2.4]heptane of claim 15, wherein $R^5$ is a phosphoramidate.

21. The spiro[2.4]heptane of claim 14, wherein $R^2$ is methyl, $R^3$ is F, and $R^4$ is $OR^7$.

22. The spiro[2.4]heptane of claim 21, wherein $R^1$ is uracil.

23. A pharmaceutical composition, comprising an effective amount of the spiro[2.4]heptane of claim 1, in a pharmaceutically acceptable carrier.

24. A pharmaceutical composition, comprising an effective amount of the spiro[2.4]heptane of claim 14, in a pharmaceutically acceptable carrier.

25. The pharmaceutical composition of claim 23, wherein the composition is suitable for oral delivery.

26. The spiro[2.4]heptane of claim 2, wherein $R^5$ is a phosphoramidate.

27. The spiro[2.4]heptane of claim 3, wherein $R^5$ is a phosphoramidate.

* * * * *